United States Patent
Koehler et al.

(10) Patent No.: US 8,026,263 B2
(45) Date of Patent: Sep. 27, 2011

(54) METHODS FOR INHIBITING NEOPROLIFERATIVE CHANGES IN BLOOD VESSEL WALLS

(75) Inventors: Ralf Koehler, Marburg (DE); Heike Wulff, Davis, CA (US); Joachim Hoyer, Marburg (DE); K. George Chandy, Laguna Beach, CA (US)

(73) Assignee: The Regents of the University of California, Oakland, CA (US)

( * ) Notice: Subject to any disclaimer, the term of this patent is extended or adjusted under 35 U.S.C. 154(b) by 912 days.

(21) Appl. No.: 10/533,060

(22) PCT Filed: Oct. 30, 2003

(86) PCT No.: PCT/US03/34837
§ 371 (c)(1),
(2), (4) Date: Mar. 12, 2007

(87) PCT Pub. No.: WO2004/039330
PCT Pub. Date: May 13, 2004

(65) Prior Publication Data
US 2009/0048270 A1   Feb. 19, 2009

Related U.S. Application Data

(63) Continuation-in-part of application No. 09/479,391, filed on Jan. 6, 2000, now Pat. No. 6,803,375.

(60) Provisional application No. 60/422,712, filed on Oct. 30, 2002.

(51) Int. Cl.
*A61K 31/425* (2006.01)
(52) U.S. Cl. ........................ 514/365; 514/372
(58) Field of Classification Search .............. 514/365, 514/372; 623/1.42
See application file for complete search history.

(56) References Cited

U.S. PATENT DOCUMENTS

| 5,358,959 | A | 10/1994 | Halperin et al. | |
| 5,556,871 | A | 9/1996 | Halperin et al. | |
| 6,613,083 | B2 * | 9/2003 | Alt | 623/1.42 |
| 6,803,375 | B1 * | 10/2004 | Chandy et al. | 514/372 |

FOREIGN PATENT DOCUMENTS

| EP | 1466902 | 12/2002 |
| WO | 97/34589 | 3/1997 |
| WO | 00/06137 | 7/1999 |
| WO | 00/07574 | 8/1999 |
| WO | 03/087101 | 4/2003 |

OTHER PUBLICATIONS

Köhler, et al., "Blockade of the Intermediate-Conductance Calcium Activated Potassium Channel as a New Therapeutic Strategy for Restenosis", Circulation, vol. 108 (2003), p. 1119-1125.

Wulff, et al., "Design of a potent and selective inhibitor of the intermediate-conductance $Ca^{2+}$-activated $K+$ channel, IKCa1: A potential immunosuppressant", PNAS, vol. 97, No. 14 (2000), p. 8151-8156.

* cited by examiner

*Primary Examiner* — Kevin E Weddington
(74) *Attorney, Agent, or Firm* — Robert D. Buyan; Stout, Uxa, Buyan & Mullins

(57) ABSTRACT

Methods, compositions and devices for inhibiting neoproliferative changes in blood vessel walls or other anatomical structures. One or more compounds of Formula I or I-A set forth herein are administered systemically and/or locally to human or veterinary patients to deter or prevent unwanted proliferative changes in blood vessels or other anatomical structures. The invention may be used to deter or prevent stenosis or restenosis of arteries following angioplasty and/or stent placement. In one embodiment, there is provided an implantable stent or stent graft from which one or more compounds of the present invention will elute or otherwise be delivered into an affected blood vessel wall.

16 Claims, 6 Drawing Sheets

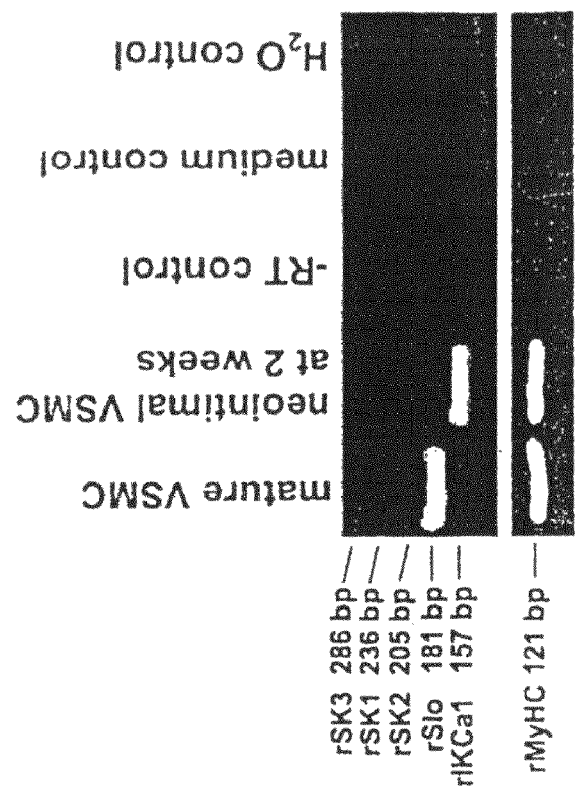
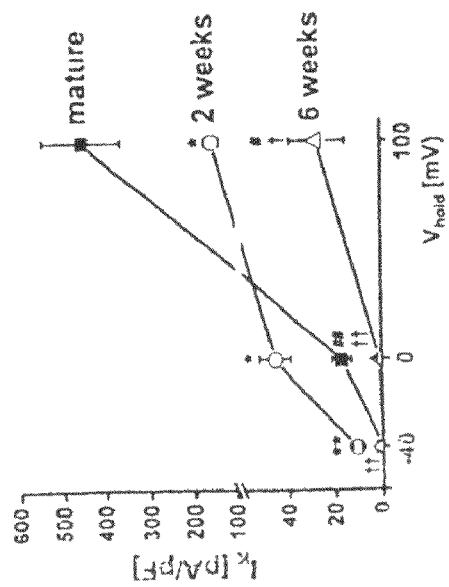

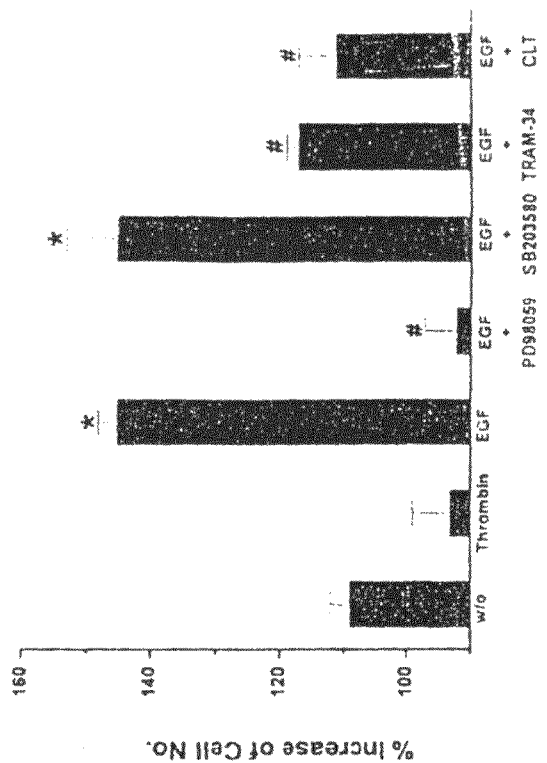
Fig. 3A
Fig. 3B

SEQUENCE LISTING

<160> NUMBER OF SEQ ID NOS: 34

<210> SEQ ID NO 1
<211> LENGTH: 19
<212> TYPE: DNA
<213> ORGANISM: Rattus sp.

<400> SEQUENCE: 1
gagaggcagg ctgtcaatg                           19

<210> SEQ ID NO 2
<211> LENGTH: 20
<212> TYPE: DNA
<213> ORGANISM: Rattus sp.

<400> SEQUENCE: 2
catcacgttc ctgaccattg                          20

<210> SEQ ID NO 3
<211> LENGTH: 20
<212> TYPE: DNA
<213> ORGANISM: Rattus sp.

<400> SEQUENCE: 3
gtgtttctcc gccttgttga                          20

<210> SEQ ID NO 4
<211> LENGTH: 20
<212> TYPE: DNA
<213> ORGANISM: Rattus sp.

<400> SEQUENCE: 4
tttaccggct gagagatgcc                          20

<210> SEQ ID NO 5

-continued

```
<211> LENGTH: 20
<212> TYPE: DNA
<213> ORGANISM: Rattus sp.

<400> SEQUENCE: 5
ggacttaggg gatggtggtt                                                   20

<210> SEQ ID NO 6
<211> LENGTH: 21
<212> TYPE: DNA
<213> ORGANISM: Rattus sp.

<400> SEQUENCE: 6
tgtgaggagt gggaggaatg a                                                 21

<210> SEQ ID NO 7
<211> LENGTH: 20
<212> TYPE: DNA
<213> ORGANISM: Rattus sp.

<400> SEQUENCE: 7
gcacacctac tgtgggaagg                                                   20

<210> SEQ ID NO 8
<211> LENGTH: 20
<212> TYPE: DNA
<213> ORGANISM: Rattus sp.

<400> SEQUENCE: 8
agctccgaca ccacctcata                                                   20

<210> SEQ ID NO 9
<211> LENGTH: 20
<212> TYPE: DNA
<213> ORGANISM: Rattus sp.

<400> SEQUENCE: 9
gctgagaaac acgtgcacaa                                                   20

<210> SEQ ID NO 10
<211> LENGTH: 20
<212> TYPE: DNA
<213> ORGANISM: Rattus sp.

<400> SEQUENCE: 10
ttggcctgat cattcacctt                                                   20

<210> SEQ ID NO 11
<211> LENGTH: 20
<212> TYPE: DNA
<213> ORGANISM: Rattus sp.

<400> SEQUENCE: 11
ggaataatgg gtgcaggttg                                                   20

<210> SEQ ID NO 12
<211> LENGTH: 20
<212> TYPE: DNA
<213> ORGANISM: Rattus sp.

<400> SEQUENCE: 12
tttgtttcca gggtgacgat                                                   20

<210> SEQ ID NO 13
```

```
<211> LENGTH: 20
<212> TYPE: DNA
<213> ORGANISM: Rattus sp.

<400> SEQUENCE: 13
cttggtggta gccgtagtgg                                              20

<210> SEQ ID NO 14
<211> LENGTH: 20
<212> TYPE: DNA
<213> ORGANISM: Rattus sp.

<400> SEQUENCE: 14
gaatttccgt tgatgcttcc                                              20

<210> SEQ ID NO 15
<211> LENGTH: 20
<212> TYPE: DNA
<213> ORGANISM: Rattus sp.

<400> SEQUENCE: 15
aacccctcca gctcttcagt                                              20

<210> SEQ ID NO 16
<211> LENGTH: 20
<212> TYPE: DNA
<213> ORGANISM: Rattus sp.

<400> SEQUENCE: 16
tgtggtaggc gatgatcaaa                                              20

<210> SEQ ID NO 17
<211> LENGTH: 20
<212> TYPE: DNA
<213> ORGANISM: Rattus sp.

<400> SEQUENCE: 17
gataaccatg cccaccagac                                              20

<210> SEQ ID NO 18
<211> LENGTH: 20
<212> TYPE: DNA
<213> ORGANISM: Rattus sp.

<400> SEQUENCE: 18
atttcagggc caacgaaaac                                              20

<210> SEQ ID NO 19
<211> LENGTH: 18
<212> TYPE: DNA
<213> ORGANISM: Rattus sp.

<400> SEQUENCE: 19
catcaatgcc aaccgcag                                                18

<210> SEQ ID NO 20
<211> LENGTH: 20
```

```
<212> TYPE: DNA
<213> ORGANISM: Rattus sp.

<400> SEQUENCE: 20
tcccgagcat ccatttcttc                                              20

<210> SEQ ID NO 21
<211> LENGTH: 20
<212> TYPE: DNA
<213> ORGANISM: Rattus sp.

<400> SEQUENCE: 21
aggccactga gagcaatgag                                              20

<210> SEQ ID NO 22
<211> LENGTH: 21
<212> TYPE: DNA
<213> ORGANISM: Rattus sp.

<400> SEQUENCE: 22
tcaataactc tacggcctcc a                                            21

<210> SEQ ID NO 23
<211> LENGTH: 19
<212> TYPE: DNA
<213> ORGANISM: Rattus sp.

<400> SEQUENCE: 23
gagaggcagg ctgtcaatg                                               19

<210> SEQ ID NO 24
<211> LENGTH: 20
<212> TYPE: DNA
<213> ORGANISM: Rattus sp.

<400> SEQUENCE: 24
gggagtcctt ccttcgagtg                                              20

<210> SEQ ID NO 25
<211> LENGTH: 20
<212> TYPE: DNA
<213> ORGANISM: Rattus sp.

<400> SEQUENCE: 25
ccagctctgt cctcagaagg                                              20

<210> SEQ ID NO 26
<211> LENGTH: 20
<212> TYPE: DNA
<213> ORGANISM: Rattus sp.

<400> SEQUENCE: 26
atggatgagc caactcaagg                                              20

<210> SEQ ID NO 27
<211> LENGTH: 21
<212> TYPE: DNA
<213> ORGANISM: Rattus sp.
```

```
<400> SEQUENCE: 27
ctgagaggca ggctgtcaat g                                      21

<210> SEQ ID NO 28
<211> LENGTH: 20
<212> TYPE: DNA
<213> ORGANISM: Rattus sp.

<400> SEQUENCE: 28
acgtgtttct ccgccttgtt                                        20

<210> SEQ ID NO 29
<211> LENGTH: 27
<212> TYPE: DNA
<213> ORGANISM: Rattus sp.

<400> SEQUENCE: 29
aagattgtct gcttgtgcac cggagtc                                27

<210> SEQ ID NO 30
<211> LENGTH: 20
<212> TYPE: DNA
<213> ORGANISM: Rattus sp.

<400> SEQUENCE: 30
tgaggccatg ggccgtgagg                                        20

<210> SEQ ID NO 31
<211> LENGTH: 19
<212> TYPE: DNA
<213> ORGANISM: Rattus sp.

<400> SEQUENCE: 31
cggcacagtc aaggctgag                                         19

<210> SEQ ID NO 32
<211> LENGTH: 21
<212> TYPE: DNA
<213> ORGANISM: Rattus sp.

<400> SEQUENCE: 32
cagcatcacc ccatttgatg t                                      21

<210> SEQ ID NO 33
<211> LENGTH: 24
<212> TYPE: DNA
<213> ORGANISM: Rattus sp.

<400> SEQUENCE: 33
cccatcacca tcttccagga gcga                                   24

<210> SEQ ID NO 34
<211> LENGTH: 20
<212> TYPE: DNA
<213> ORGANISM: Rattus sp.

<400> SEQUENCE: 34
gggatggagt ggacagagga                                        20
```

METHODS FOR INHIBITING NEOPROLIFERATIVE CHANGES IN BLOOD VESSEL WALLS

RELATED APPLICATIONS

This application is a continuation-in-part of U.S. patent application Ser. No. 09/479,391, filed Jan. 6, 2000 now U.S. Pat. No. 6,803,375. In addition, this application claims priority to U.S. Provisional Application Ser. No. 60/422,712 filed Oct. 30, 2002. The disclosures of both the above-identified patent application and the above-identified provisional patent are expressly incorporated herein by reference.

STATEMENT REGARDING FEDERALLY-FUNDED RESEARCH OR DEVELOPMENT

This invention was developed from research that was supported, at least in part, by funding under Grant Nos. MH59222 and NS14069 from the National Institutes of Health. The United States Government may have rights in this invention.

BACKGROUND OF THE INVENTION

Hyperplasia of blood vessel walls (e.g., neointimal hyperplasia, neocellullar proliferation) is believed to be an important step in the etiology of many stenotic lesions within blood vessels. In particular, neointimal hyperplasia has been identified as the primary cause of restenosis of diseased blood vessels following percutaneous balloon angioplasty and stent implantation.

Patients who suffer from diabetes have a relatively high rate of restenosis due to excessive neointimal proliferation. Additionally, in many diabetic patients, atherosclerotic disease is diffuse with ling lesions involving multiple vessels.

Currently, the treatments available to prevent restenosis following stent implantation involve either the delivery of ionizing radiation to the blood vessel wall (i.e., brachytherapy) or the delivery of antiproliferative drug such as Rapamicyn (Sirolimus) or Paclitaxel (Taxol).

Brachytherapy has been proven effective in reducing the rate of in-stent restenosis, but its use has been limited to date. Brachytherapy has been associated with untoward effects in some patients, such as subacute thrombogenicity of the irradiated blood vessel and renarrowing of the blood vessel at the edge of the stent (i.e., the "candy wrapper effect").

Antiproliferative drugs, such as rapamycin and paclitaxel, have been used systemically for purposes other than inhibition of neoproliferation of blood vessels. For example, Rapamycin (Sirolimus) inhibits T-lymphocyte activation and proliferation downstream of IL-2 and has been administered orally to deter organ transplant rejection. Paclitaxel (Taxol) inhibits mitosis and has been administered intravenously to treat a variety of cancers. When used to deter proliferative changes in blood vessels, rapamycin (Sirolimus) and paclitaxel (Taxol) are administered directly to the affected blood vessel wall by implantation of a drug eluting stent (e.g., the Cypher™ rapamycin-eluting stent manufactured by Cordis Corporation, a Division of Johnson & Johnson, Miami Lakes, Fla. and the Taxus™ paclitaxel-eluting stent manufactured by the Scimed division of Boston Scientific, Maple Grove, Minn.

Although the currently available drug eluting stents have been shown to significantly inhibit in-stent restenosis by preventing neoproliferative changes in blood vessel walls following angioplasty and stent placement, there remains a need in the art for the development of new and different agents which may be delivered locally (e.g., by a drug eluting stent or other implant or by injection into or near a blood vessel wall) or systemically (e.g., orally, transdermally, transmucosally or by injection) to deter restenosis or other neoproliferative changes in blood vessel walls.

SUMMARY OF THE INVENTION

The present invention provides compositions, preparations, methods and devices for treating or preventing vascular stenosis, restenosis (e.g., restenosis following balloon angioplasty and/or stent placement, atherectomy, in-stent restenosis, neointimal thickening, etc) or other neoproliferative changes in blood vessel walls or other anatomical structures wherein such neoproliferative changes are problematic. The antiproliferative effects of the compounds of the present invention may be mediated, at least in part, by inhibition of certain $Ca^{2+}$-activated $K^+$ channels ($K_{Ca}$) in cells of the blood vessel wall. $Ca^{2+}$-activated $K^+$ channels ($K_{Ca}$) are important regulators of vascular smooth muscle function. The intermediate-conductance $K_{Ca}$ channel encoded by the IKCa1 gene (a.k.a IK1, hSK4, KCa4 and $K_{Ca}3.1$ as per the new IUPHAR nomenclature) has been proposed to be an important regulator of cell proliferation. In human lymphocytes and fibroblasts, an up-regulation of IKCa1 expression has been shown to be an essential step in promoting cell proliferation. The present invention includes the inhibition of the intermediate-conductance $K_{Ca}$ channel encoded by the IKCa1 gene to treat, prevent or reverse vascular smooth muscle cell proliferation and/or conditions that result in whole or in part from vascular smooth muscle cell proliferation, such as atherosclerosis, vascular stenosis, vascular restenosis, etc.

In accordance with the invention, there is provided a method for deterring, inhibiting, preventing or reversing stenosis, restenosis or unwanted proliferation of cells in blood vessel walls or other anatomical structures of a human or veterinary patient by administering to the patient a therapeutically effective amount of at least one compound having the general structural formula:

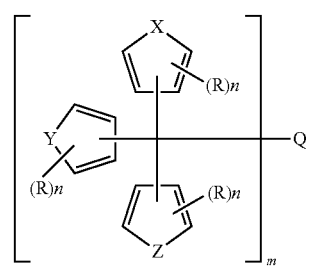

Formula I

Wherein,

X, Y and Z are same or different and are independently selected from CH2, O, S, NR₁, N═CH, CH═N and R₂—C═C—R₃, where R₂ and R₃ are H or may combine to form a saturated or unsaturated carbocyclic or heterocyclic ring, optionally substituted with one or more R groups;

$R_1$ is selected from H, alkyl, alkenyl, alkynyl, cycloalkyl, aryl, acyl and aroyl, optionally substituted with hydroxy, amino, substituted amino, cyano, alkoxy, halogen, trihaloalkyl, nitro, thio, alkylthio, carboxy and alkoxycarbonyl groups;

R is selected from H, halogen, trihaloalkyl, hydroxy, acyloxy, alkoxy, alkenyloxy, thio, alkylthio, nitro, cyano, ureido, acyl, carboxy, alkoxycarbonyl, N—$(R_4)(R_5)$ and saturated or unsaturated, chiral or achiral, cyclic or acyclic, straight or branched hydrocarbyl group with from 1 to 20 carbon atoms, optionally substituted with hydroxy, halogen, trihaloalkyl, alkylthio, alkoxy, carboxy, alkoxycarbonyl, oxoalkyl, cyano and N—$(R_4)(R_5)$ group, $R_4$ and $R_5$ are selected from H, alkyl, alkenyl, alkynyl, cycloalkyl and acyl or $R_4$ and $R_5$ may combine to form a ring, wherein a carbon may be optionally substituted by a heteroatom selected from O, S or N—$R_6$, $R_6$ is H, alkyl, alkenyl, alkynyl, cycloalkyl, hydroxyalkyl or carboxyalkyl, n is 1-5; m is 1 or 2; with the proviso that when m is 1, Q is selected from OH, CN, carboxyalkyl, N—$(R_7)(R_8)$, where $R_7$ and $R_8$ are selected from H, loWer alkyl (1-4C), cycloalkyl, aryl, acyl, amido, or $R_7$ and $R_8$ may combine to form a saturated or unsaturated heterocylic ring and optionally substituted with up to 3 additional heteroatoms selected from N, O, and S; or —NH-heterocycle, where the heterocycle is represented by thiazole, oxazole, isoxazole, pyridine, pyrimidine, and purine and where U and V are selected from H and O; and

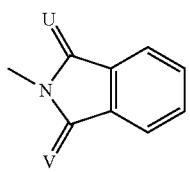

when m is 2, Q is a spacer of from 2-10 carbons as a straight or branched, chiral or achiral, cyclic or acyclic, saturated or unsaturated, hydrocarbon group, such as phenyl.

In one specific embodiment of this invention, X, Y, and Z are $R_2$—C=C—$R_3$, where: $R_2$ and $R_3$ are H; R is selected from H and halogen, preferably, F and Cl; m is 1; and Q is —N—$(R_7)(R_8)$, where $R_7$ and $R_8$ are selected from H, acyl, amido, and $R_7$ and $R_8$ combine to form a saturated or unsaturated heterocyclic ring, optionally substituted with up to three heteroatoms selected from N, O, or S, for example, pyrrolidine, piperidine, pyrazole, imidazole, oxazole, isoxazole, tetrazole, azepine, etc., which may be optionally substituted with a lower alkyl or amino group. Compounds of Formula I have been determined to selectively inhibit the intermediate-conductance calcium-activated potassium channel, IKCa1, at low nanomolar concentrations, and exhibit 200-1500 fold selectivity for this channel over other ion channels.

Further in accordance with the invention, certain presently preferred compounds of this invention having the general Formula I above include a group of triarylmethyl-1H-pyrazole compounds that have structural Formula I-A below:

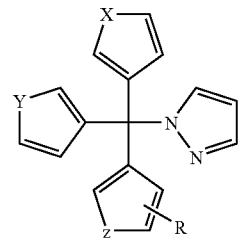

FORMULA I-A

Wherein:
X, Y, and Z are $R_2$—C=C—$R_3$, where $R_2$ and $R_3$ are H;
R is selected from H and halogen, preferably, F and Cl.

Still further in accordance with the invention, 1-[(2-chlorophenyl)diphenyl methyl]-1H-pyrazole (designated as TRAM-34) and possibly other compounds of Formulas I and I-A above and/or other pharmaceutically acceptable salts or derivatives thereof, when administered to human and/or veterinary patients, inhibit or prevent or reverse neointimal thickening or proliferation of the vascular endothelium or other cells of the walls of arteries. Appendix A, which forms a part of this patent application, lists a number of examples of compounds of the present invention, including TRAM 34.

Still further in accordance with the invention, there is provided a method for deterring, inhibiting, preventing or reversing stenosis, restenosis or unwanted proliferation of cells in blood vessel walls or other anatomical structures in a human or veterinary patient comprises administering to the patient a therapeutic amount of a compound having Formulas I or I-A above and/or other pharmaceutically acceptable salts or derivatives thereof. The step of administration may be carried out in a number of ways, including any feasible systemic or local route of administration. The compounds may be delivered systemically by oral, transdermal or transmucosal delivery or by injection (e.g., intravenous, intramuscular, subcutaneous, etc.) The compounds may be delivered locally (e.g., to an affected region of a blood vessel wall) by direct injection into or near the affected blood vessel wall or by placement or implantation of a permanent or temporary device (e.g., a stent or stent graft) from which the compound elutes or otherwise travels into the affected blood vessel wall in an amount that is effective to deter or prevent unwanted neoproliferative changes.

Still further in accordance with the invention, there are provided implantable devices (e.g., stents, stent-grafts, etc.) which contain, are coated with or otherwise include one or more compounds of Formulas I or I-A above and/or other pharmaceutically acceptable salts or derivatives thereof such that the compound(s) will elute or otherwise travel from the implanted device to tissue (e.g., an artery wall) in an amount and concentration that is effective to deter or prevent neoproliferative changes (e.g., stenosis, restenosis, in-stent restenosis, atherogenesis, etc.) in that tissue.

Further aspects and objectives of the present invention will be apparent to those of skill in the art upon reading of the detailed description and examples set forth herebelow.

BRIEF DESCRIPTION OF THE DRAWINGS

FIG. 1c is a graph showing the results of quantitative analysis of $IK_{Ca}$ and $BK_{Ca}$ currents in mature VSMC (■) and neointimal VSMC at two (○) and six weeks (Δ) at holding potentials of −40, 0, and +100 mV. Values are given as mean±SE; *P<0.05, **P<0.01, neointimal VSMC at two weeks vs. mature VSMC; # P<0.05, ## P<0.01 neointimal VSMC at six weeks vs. mature VSMC; † P<0.05, †† P<0.01 neointimal VSMC at six weeks vs. neointimal VSMC at two weeks; Wilcoxon Rank-Sum test.

FIG. 2a shows Ethidium bromide-stained gels of RT-PCR products of $K_{Ca}$ genes (upper panel) and rMyHC (lower panel) in single mature and neointimal VSMC at two weeks after BCI and negative controls: one -RT control, one medium sample, and $H_2O$-control.

FIG. 3a shows the results of patch-clamp and RT-PCR analysis of rIkca1 expression following EGF stimulation in A7r5 cells. The left panel shows representative $K_{Ca}$ currents in unstimulated (w/o) and EGF-stimulated cells (48 h) in the absence or presence of the MEK-inhibitor PD98059. The right panel shows an ethidium bromide-stained gel (right) of real-time RT-PCR products of rIKCa1 in unstimulated and EGF-stimulated cells with or without PD98059 (20 μM) or the p38-MAP kinase inhibitor SB203580 (5 μM).

FIG. 3b is a graph comparing the percent cell increase in cell number 48 hours after treatment with various compounds. Conditions: thrombin (n=6), EGF (n=13), EGF+PD98059 (n=7), EGF+SB203580 (n=5), EGF+TRAM-34 34 (n=6), EGF+CLT (n=6). Values are given as mean±SE; *P<0.01 vs. w/o, # P<0.001 vs. EGF, Wilcoxon Rank-Sum test.

DETAILED DESCRIPTION AND EXAMPLES

Figure 1A:
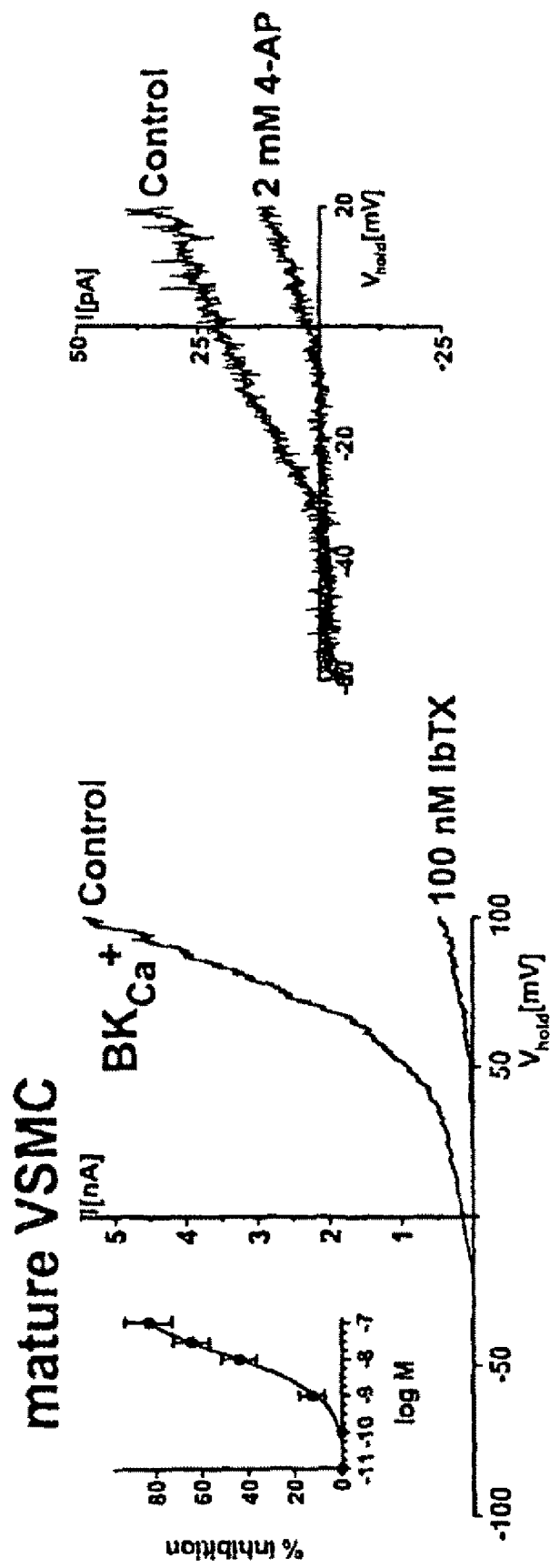
FIG. 1a is a set of graphs showing $BK_{Ca}$-currents in mature VSMC elicited through dialysis with 3 μM free $Ca^{2+}$ and blocked by 100 nM IbTX (left panel), and voltage-gated $K^+$ currents in mature VSMC recorded with a $Ca^{2+}$ free pipette solution and blockaded by 4-AP (right panel). The left panel includes an inset showing the concentration-dependent blockade of $BK_{Ca}$-currents by IbTX (n=4-5).

The following detailed description, and the examples contained therein, are provided for the purpose of describing and illustrating certain embodiments of the invention only and are not intended to limit the scope of the invention in any way.

The present invention provides for the use of therapeutically effective substituted triaryl methane compounds that are more selective in inhibiting the said channel in nanomolar concentrations and exhibiting no inhibitory effect on the cytochrome P-450-dependent enzyme systems at these concentrations. Because the imidazole moiety is responsible for inhibition of cytochrome P-450-dependent enzymes, applicants have synthesized compounds of Formula I and I-A above that do not include the imidazole moiety, including instead other heterocyclic groups. Applicants have also synthesized a range of triaryl-methanols, amines, ureas, acetonitriles and related compounds, as listed in Appendix A, by synthetic methodologies outlined in Scheme 1 below. The triarylmethyl-1-H-pyrazoles of this invention potently block IKCa1. Applicants have further discovered that one particular compound of this invention having Structural formula I-B below, exhibits ~3-fold greater affinity for the channel ($K_d$=20 nM) than Clotrimazole ($K_d$=70 nM), and does not inhibit cytochrome P450 3A4, the major xenobiotic metabolizing enzyme in the human liver, even at a concentration of 10 μM.

Furthermore, applicants have discovered that the ratio of cytochrome P-450-dependent enzyme systems inhibition ($EC_{50}$) to IKCa1 inhibition ($K_d$) needs to be >50-100 to achieve the therapeutic effect for prevention of the diseases modulated by IKCa1 channel without the aforementioned side effects evident in clotrimazole and related imidazoles.

As a further test of selectivity, applicants have evaluated 1-[(2-chlorophenyl)diphenylmethyl]-1H-pyrazole, one of the compounds of this invention (also known as TRAM-34, and designated as T-34 in Appendix A), on other cloned and native ion channels, (Kv1.1-1.5, Kv3.1, Kv4.2, Jurkat-$SK_{Ca}$, BKCa, hSKM1-Na, CRAC and lymphocyte chloride channels. All of these channels Were blocked with $K_d$ values ~5 □M. Thus, TRAM-34 was found to be a remarkably potent and selective IKCa1 inhibitor. Because of its structural similarity to clotrimazole and based on experimental data described in the examples below, Applicants expect that TRAM-34 (logP=4.0 versus 3.5 for clotrimazole) will have a similar or slightly better bioavailabity than clotrimazole and, contrary to clotrimazole, no side effects mediated by inhibition of cytochrome P450-dependent enzymes.

The invention is particularly concerned with compositions, preparations, methods and apparatus for treating or preventing vascular stenosis or proliferation of vascular endothelium in human or veterinary patients, and further with such methods and apparatus which are devoid of side effects associated with currently available drugs on the market.

Compounds Useable in Accordance with this Invention:

The compounds of this invention are generally represented by Formula I shown above.

In another preferred embodiment having the general Formula I, X, Y, and Z are each $R_2$—C≡C—$R_3$ (where $R_2$ and $R_3$ are H; R is selected from H and halogen, preferably, F and Cl); m is 2; and Q is a spacer of from 2-10 carbons either as a straight or branched hydrocarbon chain, or containing a hydrocarbon ring such as phenyl. Some of the preferred compounds covered by this embodiment include:

N,N-1,2-ditritylamino ethane (T21)
1,4-ditritylaminomethyl benzene (T23)
N,N-1,3-[(2-chlorophenyl)diphenylmethyl]amino propane (T49).

Further in accordance with the invention, preferred compounds of this invention having the general Formula I above, are a group of triarylmethyl-1H-pyrazole compounds that have structural Formula I-A below:

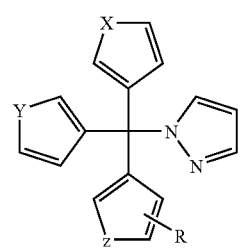

FORMULA I-A

Wherein:

X, Y, and Z are $R_2$—C=C—$R_3$, where $R_2$ and $R_3$ are H;
R is selected from H and halogen, preferably, F and Cl;
Preferred compounds covered by Formula I-A include,
1-[(2-chlorophenyl)diphenylmethyl]-1H-pyrazole (T34)
1-[(2-fluorphenyl)diphenylmethyl]-1H-pyrazole (T46)
1-[(4-chlorophenyl)diphenylmethyl]-1H-pyrazole (T13)
1-[(2-fluorphenyl)diphenylmethyl]-1H-pyrazole (T28)

B. Synthesis of the Compounds

The compounds of this invention may be prepared as outlined in Scheme 1 and Example 1. The individual steps are described below in the examples. The synthetic procedures described here are exemplary and may be modified by those skilled in the art.

intestinal and parenteral administration, including intramuscular, subcutaneous and intravenous injections. In addition, the compounds may be delivered locally (e.g., to an affected region of a blood vessel wall) by direct injection into or near the affected blood vessel wall or by placement or implantation of a permanent or temporary device (e.g., a stent or stent graft) from which the compound elutes or otherwise travels into the affected blood vessel wall in an amount that is effective to deter or prevent unwanted neoproliferative changes.

The compounds described herein, or pharmaceutically acceptable salts or hydrates thereof, may be administered singly or in combination with other therapeutic agents, e.g. analgesics, antibiotics, non-steroidal anti-inflammatory agents, steroids, and other immunosuppressive drugs like cyclosporin A, rapamycin, FK506 or Kv1.3 selective blockers. At least one of the preferred compounds, 1-[(2-chlo-

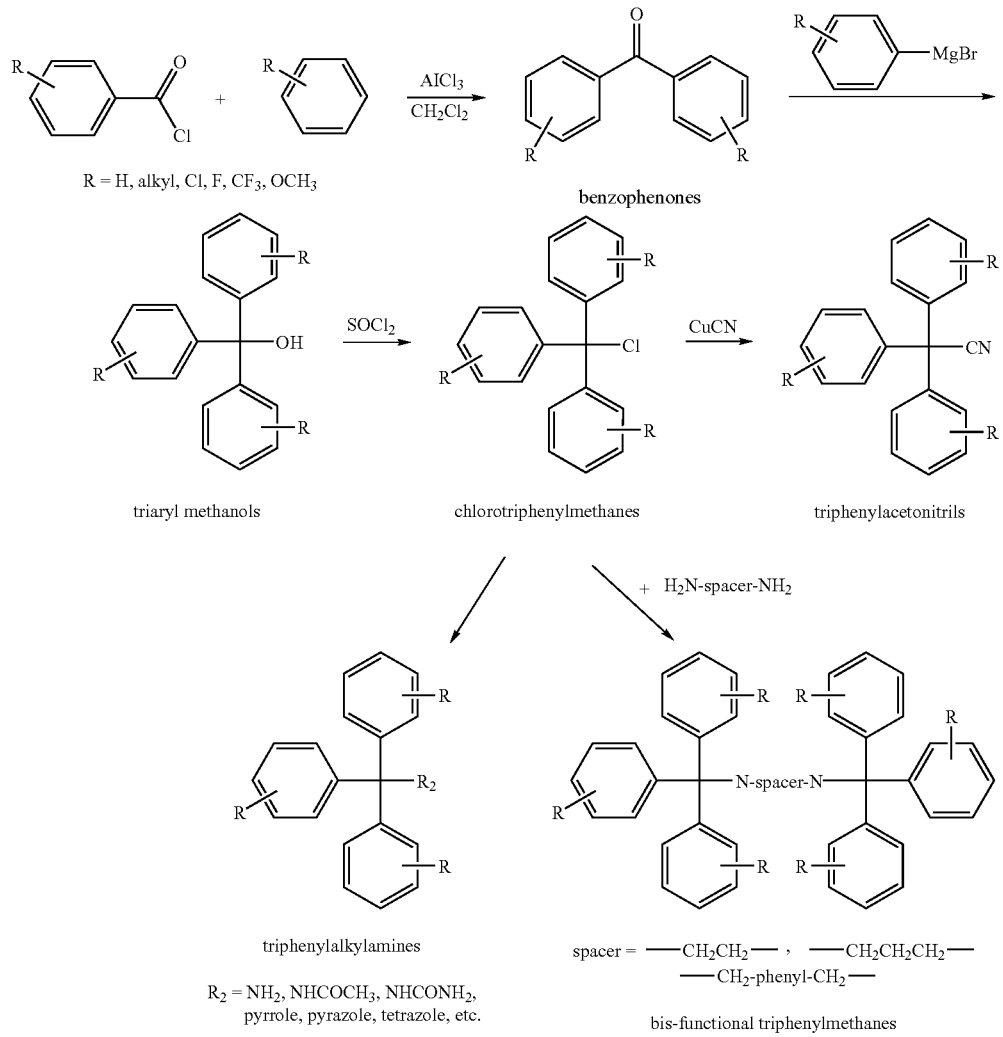

C. Preferred Routes of Administration

The compounds described herein, or pharmaceutically acceptable salts or hydrates thereof, can be delivered to a patient using a wide variety of routes or modes of administration. Suitable routes of administration include, but are not limited to, inhalation, transdermal, oral, rectal, transmucosal, rophenyl)diphenylmethyl]-1H-pyrazole designated as T34 in Appendix A, may be administered per se or in the form of a pharmaceutical composition wherein the active compound is in admixture with one or more physiologically acceptable carriers, excipients or diluents. Pharmaceutical compositions for use in accordance with the present invention may be formulated in conventional manner using one or more physiologically acceptable carriers comprising excipients and auxiliaries, which facilitate processing of the active compounds into preparations, which can be used pharmaceutically. Proper formulation is dependent on the route of administration chosen. For parenteral administration (bolus injection or continuous infusion), the agents of the invention may be formulated in water-soluble form in aqueous solutions, preferably in physiologically compatible buffers such as Hank's solution, Ringer's solution, or physiological saline buffer. Additionally, suspensions of the compounds may be prepared as oily injections with fatty oils, synthetic fatty acid esters, or liposomes. The compounds may also be formulated as a depot preparation. For oral administration, the compounds can be formulated readily by combining the active compound with pharmaceutically acceptable carriers well known in the art. Such carriers enable the compounds of the invention to be formulated as tablets, pills, dragees, capsules, liquids, gels, syrups, slurries, suspensions and the like, for oral ingestion for patients to be treated. Suitable excipients are, in particular, fillers such as sugars, including lactose, sucrose, mannitol, or sorbitol: cellulose preparations such as, for example maize starch, wheat starch, rice starch, potato starch, gelatin, gum tragacanth, methyl cellulose, hydroxypropyl-methylcellulose, sodium carboxymethylcellulose, and/or polyvinylpyrrolidone.

Figure 4:
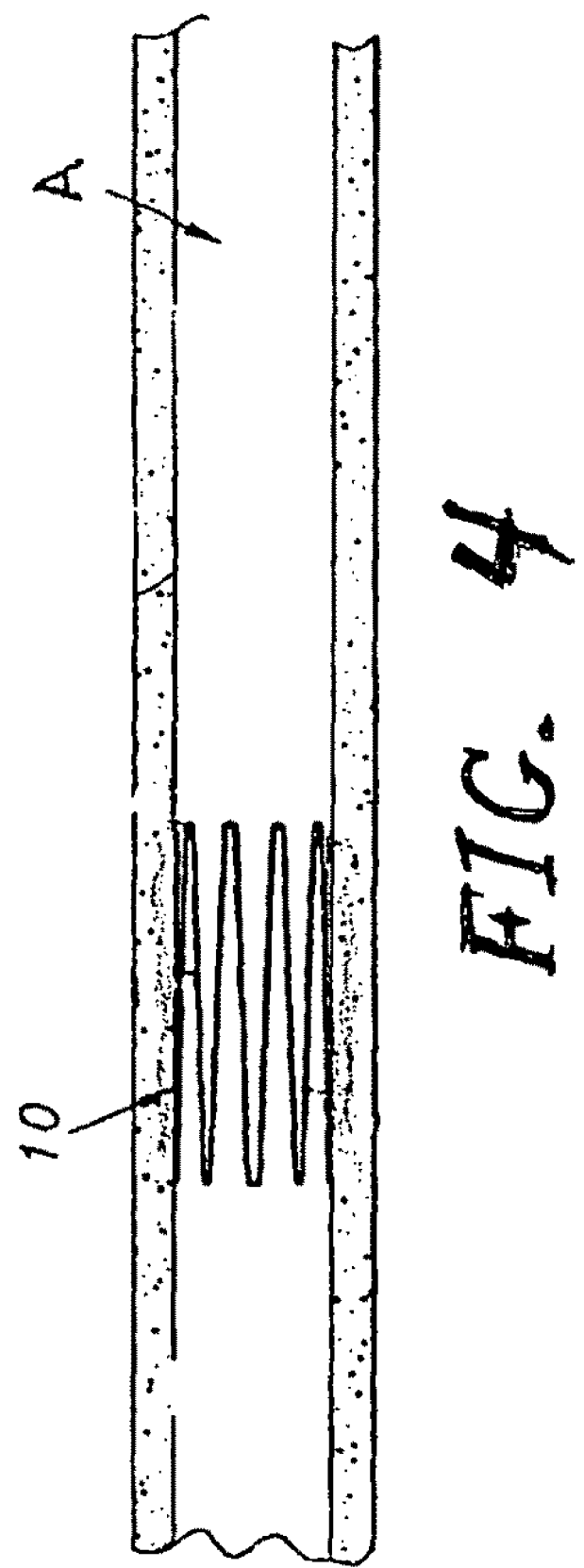
FIG. 4 is a longitudinal sectional view of an artery having a compound-eluting stent of the present-invention positioned therein.

As an alternative to aforementioned routes of administration, a coating 10 formed of, or containing, any of the compounds of the invention may be formed on or applied to the surface of a stent 12 or other implantable device to be inserted in, on, or near a patient's blood vessel 14, as shown in FIG. 4.

C. Examples

The following examples serve to illustrate various aspects of the invention and are not to be construed as limiting the invention to those embodiments so exemplified.

Example 1

Synthesis of Triarylmethanols

General Method A 25 mmol of magnesium turnings and a catalytic amount of iodine to initiate the reaction were stirred in 50 ml of anhydrous diethyl ether. Then, a solution containing 25 mmol of the appropriate aryl bromide in anhydrous diethyl ether (50 ml) was slowly added allowing a gentle reflux. Once the addition was complete the mixture was heated at reflux until all the magnesium was consumed. Next, a solution of the required benzophenone (25 mmol) in anhydrous diethyl ether (50 ml) was slowly added. The resulting mixture was heated at reflux for 5-12 h, then cooled to 0° C. and poured into 100 ml of cold water. To dissolve the precipitating magnesium hydroxide the mixture was acidified with concentrated HCl. The organic phase was separated, and the aqueous phase was extracted with diethyl ether. The combined organic phases were washed with sodium bicarbonate solution (10%) and then dried over sodium sulfate. Evaporation of the solvent gave the respective triarylmethanol either as creamy solid or as an oil, which normally was recrystallized from petroleum ether (40-60° C.) several times.

Example 2

Preparation of (2-Chlorophenyl)diphenyl Methanol

Compound T3

Following the procedure outlined in Example 1, 1.3 g (52 mmol) of magnesium turnings, 10.0 g (52 mmol) of 1-bromo-2-chlorobenzene and 9.4 g (52 mmol) benzophenone gave 9.81 g (64%) of (2-Chlorophenyl) diphenyl methanol (Compound T3), mp: 91° C.

Example 3

Following the procedure outlined in Example 1, the following triarylmethanols (Table 1) were prepared.

TABLE 1

| Triarylmethanol Compound | Designation on Appendix A | Yield | Melting Point |
| --- | --- | --- | --- |
| (4-Chlorophenyl)diphenyl methanol | T1 | 56% | 82° C. |
| (3-Chlorophenyl)diphenyl methanol | T2 | 52% | 53° C. |
| Bis-(4-chlorophenyl)phenyl methanol | T4 | 56% | 86° C. |
| Bis-(3-chlorophenyl)phenyl methanol | T5 | 52% | oil |
| (2-Thienyl)diphenyl methanol | T9 | 64% | 129° C. |
| (4-Fluorophenyl)diphenyl methanol | T12 | 58% | 120.5° C. |
| (4-Fluorophenyl)(2-thienyl)phenyl methanol | T14 | 62% | 75° C. |
| Bis-(4-methoxyphenyl)phenyl methanol | T15 | 62% | sticky dark red paste |
| Tris-(4-methoxyphenyl) methanol | T16 | 48% | 75° C. |
| Di-(2-thienyl) phenyl methanol | T35 | 54% | 86° C. |
| (2-Fluorophenyl)diphenyl methanol | T36 | 69% | 116° C. |
| (2-Chlorophenyl)(2-thienyl)phenyl methanol | T43 | 58% | 90.5° C. |
| Diphenyl(2-trifluoromethylphenyl) methanol | T54 | 57% | 111° C. |
| Diphenyl(4-trifluoromethylphenyl) methanol | T55 | 68% | oil |
| Diphenyl(3-trifluoromethyl-phenyl) methanol | T56 | 62% | 52° C. |

Example 4

Synthesis of Triaryl Chlorides

General Method B

To a stirred suspension of 20 mmol of the corresponding triarylmethanol in 100 ml of petroleum ether (40-60° C.) was added dropwise an excess of freshly distilled thionyl chloride. The reaction mixture was stirred at room temperature for 30 min and then heated under reflux for 1 h. Excess thionyl chloride was removed by concentrating to dryness in vacuo. The residue was suspended in 100 ml of petroleum ether and left in the refrigerator overnight. The resulting crystals were filtered off and thoroughly washed with petroleum ether. To avoid hydrolysis of these sensitive triaryl chlorides, they were immediately used for further reactions after being characterized by melting point and mass spectrometry.

Example 5

Synthesis of (2-Chlorophenyl)diphenyl Chloromethane

Following the procedure outlined in Example 4, 5.00 g (17.1 mmol) of (2-chlorophenyl) diphenyl methanol, designated as T-3 on Appendix A, was treated with 2.5 ml thionyl chloride (34 mmol) according to general method B to give 4.39 g (82%) of (2-Chlorophenyl) diphenyl chloromethane, mp: 131° C.

Example 6

Synthesis of Triarylmethylamines

General Method C

To a solution of the appropriate triaryl chloride (5 mmol) in anhydrous acetonitrile (100 ml) Were added the desired amine or urea (5 mmol) and triethylamine (5 mmol) as proton acceptor. The resulting mixture was stirred and heated at reflux for 24 h. Evaporation of the solvent afforded a creamy residue, which was dissolved in 200 ml of methylene chloride. The mixture was washed two times with 50 ml of water, dried over $Na_2SO_4$, and concentrated in vacuo. The crude product was recrystallized from petroleum ether (40-60° C.)/methylene chloride.

Example 7

Preparation of 1-Tritylpyrrolidine

Compound T7

2.00 g (7.2 mmol) of trityl chloride was treated with 0.51 g (7.2 mmol) pyrrolidine and 0.72 g (7.2 mmol) triethylamine according to General Method C in Example 6 to give 1.86 g (82%) of 1-Tritylpyrrolidine (T7), mp: 126° C.

Example 8

Following the procedure in Example 6, the following compounds (Table 2) Were prepared.

TABLE 2

| Triarylmethylamines from an amine or urea | Number | Yield | Melting Point |
|---|---|---|---|
| 1-Trityl-1H-pyrrole | T10 | 79% | 243° C. |
| N-trityl urea | T24 | 58% | 238° C. |
| N-[(4-chlorophenyl) diphenyl methyl] urea | T29 | 62% | 228° C. |
| N-[(4-fluorophenyl) diphenyl methyl] urea | T31 | 66% | 222° C. |
| N-[(2-chlorophenyl) diphenyl methyl] urea | T33 | 68% | 243° C. |

TABLE 2-continued

| Triarylmethylamines from an amine or urea | Number | Yield | Melting Point |
|---|---|---|---|
| 1[(2-Chlorophenyl) diphenyl methyl]-1H-pyrrole | T44 | 67% | 184° C. |
| N-[(2-fluorophenyl) diphenyl methyl] urea | T45 | 66% | 225° C. |

Example 9

Synthesis of Triarylmethylamines with a Heterocyclic Amine

General Method D

Especially with substituted pyrazoles and pyrimidines General Method C tended to give unsatisfactory yields and oily, dark byproducts, which where extremely difficult to remove even by column chromatography. Therefore excessive amine was used as a hydrogen acceptor instead of triethylamine. To a solution of the required triaryl chloride (5 mmol) in anhydrous acetonitrile (100 ml) was added an excess of the required amine (10-20 mmol). After stirring under reflux for 8 h the mixture was poured into cold water (400 ml) and kept at 4° C. for 2 h. The precipitate formed was collected by vacuum filtration, thoroughly washed with water to remove any of the remaining amine, and recrystallized from ethanol.

Example 10

Preparation of 1-[(2-Chlorophenyl)diphenyl methyl]-1H-pyrazole

Compound T34

1.50 g (4.8 mmol) of 2-chlorotrityl chloride obtained under Example 5 was reacted with 1.00 g (15 mmol) of pyrazole according to general method D to give 1.26 g (76%) of 1-[(2-Chlorophenyl) diphenyl methyl]-1H-pyrazole, mp: 135° C.

Example 11

Following the procedure in Example 9, the following compounds (Table 3) were prepared.

TABLE 3

| Triarylmethylamines from Heterocyclic Amines | Designation on Appendix A | Yield | Melting Point |
|---|---|---|---|
| 1-Trityl-1H-pyrazole | T11 | 82% | 202° C. |
| 1[(4-Chlorophenyl)diphenylmethyl]-1H-pyrazole | T13 | 87% | 133° C. |
| 1-[Tris(4-methoxyphenyl)methyl]-1H-pyrazole | T19 | 82% | 158° C. |
| 1-[(4-Fluorophenyl)diphenylmethyl]-1H-pyrazole | T28 | 84% | 145° C. |
| 1-[Diphenyl(2-thienyl)methyl]-1H-imidazole | T37 | 78% | 176° C. |
| 1-[Diphenyl(2-thienyl)methyl]-1H-pyrazole | T38 | 83% | 157° C. |
| 1-[(2-Fluorophenyl)diphenylmethyl]-1H-pyrazole | T46 | 84% | 192° C. |
| N-(1,3-thiazol-2yl)-N-tritylamine | T57 | 79% | 213° C. |
| 1-{Diphenyl[2-(trifluoromethyl)phenyl]methyl}-1H-pyrazole | T58 | 46% | 114° C. |
| 1-{Diphenyl[2-(trifluoromethyl)phenyl]methyl}-3-(trifluoromethyl)-1H-pyrazole | T59 | 62% | 107° C. |
| 1-{Diphenyl[4-(trifluoromethy})phenyl]methyl}-1H-pyrazole | T60 | 65% | 135° C. |
| N-Diphenyl[4-(trifluoromethyl)phenyl]methyl-N-(1,3-thiazol-2-yl)amine | T61 | 58% | 166° C. |
| 1-[(2-Chlorophenyl)diphenylmethyl]-3,5-dimethyl-1H-pyrazole | T62 | 68% | 195° C. |
| 1-[(2-Chlorophenyl)diphenylmethyl]-3-methyl-1H-pyrazole | T63 | 78% | 118° C. |
| N-[(4-Chlorophenyl)diphenylmethyl]-N-(1,3-thiazol-2yl)amine | T64 | 62% | 156° C. |
| 1-[{2-Chlorophenyl)diphenylmethyl]-3-(trifluoromethyl)-1H-pyrazole | T65 | 64% | 139° C. |
| N-[(2-Chlorophenyl)diphenylmethyl]-N-(1,3-thiazol-2yl)amine | T66 | 72% | 152° C. |

TABLE 3-continued

| Triarylmethylamines from Heterocyclic Amines | Designation on Appendix A | Yield | Melting Point |
|---|---|---|---|
| N-[(2-Chlorophenyl)diphenylmethyl]-N-(4-pyridyl)amine | T67 | 92% | 115° C. |
| N-[(2-Chlorophenyl)diphenylmethyl]-N-(2-pyrimidyl)amine | T68 | 64% | 162° C. |
| N-[(2-Chlorophenyl)diphenylmethyl]-N-(2-pyridyl)amine | T69 | 67% | 115° C. |
| N-[(4-Chlorophenyl)diphenylmethyl]-N-(4-pyridyl)amine | T70 | 81% | 214° C. |
| 2-[(2-Chlorophenyl)diphenylmethyl]-1H-isoindole-1,3(2H)-dione | T71 | 67% | 168° C. |
| N-Diphenyl[2-(trifluoromethyl)phenyl]methyl-N-(1,3-thiazol-2yl)amine | T72 | 65% | 164° C. |
| N-Diphenyl[2-(trifluoromethyl)phenyl]methyl-N-(2-pyrimidinyl)amine | T73 | 78% | 133° C. |
| N-[(2-Fluorophenyl)diphenylmethyl]-N-(1,3-thiazol-2yl)amine | T78 | 58% | 169° C. |
| N-[(2-Chlorophenyl)diphenylmethyl]-N-(4-methyl-1,3-thiazol-2yl)amine | T79 | 49% | 168° C. |
| N-{5-[(4-Nitrophenyl)sulfonyl]-1,3-thiazol-2yl}-N[(2-chlorophenyl)(diphenyl)methyl]amine | T81 | 73% | 135° C. |
| 1-[(2-Chlorophenyl)diphenylmethyl]-1H-1,2,3,4-tetrazole | T84 | 72% | 129° C. |
| 1-[(2-Chlorophenyl)diphenylmethyl]-1H-1,3-benzimidazole | T85 | 68% | 168° C. |

Example 12

Preparation of N,N-1,2-ditritylamino Ethane

Compound T21

2.0 g (7.2 mmol) of trityl chloride, 0.21 g (3.6 mmol) of 1,2-diaminoethane and 0.72 g (7.2 mmol) of triethyl amine Were dissolved in methylene chloride and heated under reflux for 8 hours as described under Example 6 (Ng 1995, *Tetrahedron* 51: 7883) to yield 1.03 g (53%) of N,N-1,2-ditritylamino ethane, mp: 172° C.

Example 13

The procedure in Example 12 was followed to obtain the following compounds (Table 4).

TABLE 4

| Bis-triarylmethyldiamines from Diamines | Number | Yield | Melting Point |
|---|---|---|---|
| N,N-1,3-Ditritylamino propane | T22 | 58% | 179° C. |
| 1,4-Ditritylaminomethyl benzene | T23 | 64% | 201° C. |
| N,N-1,2-[(2-Chlorophenyl)diphenylmethyl] amino ethane | T48 | 62% | 228° C. |
| N,N-1,3-[(2-Chlorophenyl)diphenylmethyl] amino propane | T49 | 58% | 198° C. |

Example 14

Preparation of (2-chlorophenyl)diphenylmethyl Amine

Compound T41

To a solution of 1.50 g (4.79 mmol) of (2-Chlorophenyl) diphenyl chloromethane, obtained under Example 5, in 100 ml of ethyl ether was added 100 ml of 25% ammonia solution and the resulting mixture was vigorously stirred at room temperature for 24 hours (Casadio 1973, *J. Pharm. Sci.* 62: 773). The organic layer was separated and the aqueous layer was extracted with ether. The combined organic phases were thoroughly washed with water, dried over anhydrous sodium sulfate and evaporated to dryness. The oily residue was crystallized from petroleum ether (40-60° C.) to give 1.10 g (78%) of the product, mp: 98° C.

Example 15

Following the procedure set forth in Example 14, the following three compounds were prepared (Table 5).

TABLE 5

| Triarylmethylamines from Ammonia | Number | Yield | Melting Point |
|---|---|---|---|
| (4-Fluorophenyl) diphenylmethyl amine | T42 | 81% | 62° C. |
| (2-Fluorophenyl) diphenylmethyl amine | T47 | 79% | 84° C. |
| (2-Trifluoromethylphenyl) diphenylmethyl amine | T82 | 62% | 106° C. |

Example 16

Preparation of N-(2-chlorophenyl)diphenylmethyl Acetamide (T75)

2.5 g (8.51 mmol) of (2-chlorophenyl) diphenylmethyl amine obtained under Example 14 was acetylated with 30 ml of freshly distilled acetic anhydride. The resulting mixture was stirred at 40° C. for 4 hours, poured into 200 ml of cold water and left in the refrigerator overnight. The precipitate was collected by vacuum filtration and recrystallized from ethanol to yield 1.17 g (41%) of the product, mp: 181° C.

Example 17

Following the procedure in Example 16 the following N-triarylmethyl acetamides were prepared from the corresponding amines obtained under Example 15 (Table 6).

TABLE 6

| N-Triarylmethylacetamides from corresponding Amines | Number | Yield | Melting Point |
|---|---|---|---|
| N-(2-Fluorophenyl)diphenylmethyl acetamide | T76 | 73% | 215° C. |
| N-(2-Trifluoromethylphenyl)diphenylmethyl acetamide | T83 | 83% | 185° C. |

Example 18

Preparation of 2-(4-Chlorophenyl) 2,2-diphenylacetonitrile (T26)

2-(4-Chlorophenyl) 2,2-diphenylacetonitrile was synthesized by carefully triturating 1.50 g (4.8 mmol) of 4-chlortrityl chloride with 1.00 g (11 mmol) of copper cyanide and the resulting mixture was heated for 4 hours at 150° C. without a solvent. After cooling 50 ml of toluene was added, the mixture was filtered and the filtrate was concentrated in vacuo. The resulting residue was recrystallized from petroleum ether (40-60° C.) to give 0.66 g (45%) of the triarylmethyl acetonitrile derivative.

Example 19

The following triarylmethyl acetonitriles were prepared by the procedure outlined in Example 18 (Table 7).

TABLE 7

| Triarylmethylacetonitriles from corresponding Chlorides | Number | Yield | Melting Point |
|---|---|---|---|
| 2-(4-Fluorophenyl) 2,2-diphenylacetonitrile | T27 | 52% | 76° C. |
| 2-(2-Chlorophenyl) 2,2-diphenylacetonitrile | T39 | 52% | 143° C. |
| 2-(2-Fluorophenyl) 2,2-diphenylacetonitrile | T40 | 63% | 144° C. |

Compounds T39 and T40 have been disclosed in Brugnara, PCT Application WO 97/34589. Compounds T50 (4-pyridyl, diphenyl methanol), T51 (2,2,2-Triphenyl propionic acid), T52 [(S)-(−)-α,α-Diphenyl-2-pyrrolidine methanol] and T53 [(R)-(+)-α,α-Diphenyl-2-pyrrolidine methanol] used in the biological testing are commercially available from Aldrich Chemical. Co., Milwaukee, Wis. 53201, USA The following examples provide exemplary, not limiting, formulations, for administering the compounds of the invention to mammals. Any of the compounds described herein, or pharmaceutically acceptable salts or hydrates thereof, may be formulated as illustrated in the following examples.

Example 20

| Tablet Formulation Tablets each containing 50 mg of active ingredient are made up as follows: | |
|---|---|
| Compound T34 | 50 mg |
| Starch | 45 mg |
| Microcrystalline cellulose | 45 mg |
| Sodium carboxymethyl starch | 4.5 mg |
| Talc | 1 mg |
| Polyvinylpyrrolidone (10% in water) | 4 mg |
| Magnesium Stearate | 0.5 mg |
| | 150 mg |

Tablets can be prepared from the ingredients listed by wet granulation followed by compression. The active ingredient, starch and cellulose are passed through a No. 45 mesh U.S. sieve and are mixed thoroughly. The solution of PVP is mixed with the resultant powders, which are then passed through a No. 14 mesh U.S. sieve. The granules are dried at 50°-60° C. and passed through a No. 18 mesh U.S. sieve. The sodium carboxymethyl starch, magnesium stearate and talc, previously passed through a no. 60 mesh U.S. sieve, are then added to the granules, which after mixing are compressed by a tablet machine to yield tablets each weighing 150 mg.

Example 21

| Gelatin Capsules Hard gelatin capsules are prepared using the following ingredients: | |
|---|---|
| Compound T34 | 100 mg/capsule |
| Starch dried | 200 mg/capsule |
| Magnesium stearate | 10 mg/capsule |

The above ingredients are mixed and filled into hard gelatin capsules in 310 mg quantities.

Example 22

Reduction of Neointimal Thickening in Subjects Treated with TRAM-34 vs. Clotrimazole Applicants investigated the ability of clotrimazole and its more selective derivative TRAM-34 to reduce neointima formation in vivo following balloon catheter injury (BCI). The study was performed as follows:

Animals. Three to four month-old male Sprague-Dawley rats (350-450 g) were purchased from the Animal Breeding Center Schönewalde GmbH (Schönewalde, Germany).

Cell line. Commercially available rat aortic VSMC (A7r5) were cultured in DMEM containing 1 mM sodium pyruvate, non-essential amino acids, penicillin, (20 units/ml), streptomycin (20 Δg/ml), and 10% fetal calf serum (all Biochrom KG, Berlin, Germany).

Reagents. PD98059 and SB203580 were obtained from TOCRIS (Ballwin, Mo.). TRAM-34 (1-[(2-chlorophenyl) diphenylmethyl]-1H-pyrazole) was synthesized as described in this invention; TRAM-34 was dissolved in dimethyl sulfoxide for in vitro assays and in peanut oil for in vivo administration. sEGF was obtained from Biochrom KG Berlin, Germany. All other chemicals and toxins were obtained from Sigma (Deisenhofen, Germany).

Balloon catheter injury and treatment protocols. Under the aegis of an animal study protocol approved by the Animal Care and Use Committee of the Freie Universität, Berlin, rats were subjected to BCI of the left carotid artery (CA) by use of a 2F Fogarty embolectomy catheter (Baxter Scientific, Irvine, Calif.). Rats were sacrificed two weeks (n=5) and six weeks (n=6) after BCI, and left and right CA were excised. Separate groups of rats (each n=4-11) were treated with daily subcutaneous injections of TRAM-34 (120 mg/kg) or the vehicle (peanut oil) for one, two, and six weeks after BCI. Another group (n=7) was treated with CLT (120 mg/kg) for two Weeks after BCI. TRAM-34 and CLT serum levels were quantitatively determined by a bioassay as described previously (10).

Neointimal thickening was determined at one, two, and six weeks after BCI in paraffin embedded and differential non-serial cross sections stained with hematoxylin and eosin to visualize nuclei and cytoplasm, or with Sirius Red to detect collagen. Cross sectional areas of the neointimal and medial smooth-muscle-cell layers, the neointima/media ratio, and collagen content were calculated with a computerized analysis system (Scion Image, Scion Corporation, Frederick, Md.). Analysis was done in a blinded manner.

Patch-clamp experiments. All experiments were conducted in the whole-cell configuration of the patch-clamp technique. If not otherwise stated, cells were dialyzed with a pipette solution containing (mM): 135 KCl, 4 $MgCl_2$, 1 EGTA, 0.955 $CaCl_2$, ($[Ca^{2+}]_{free}$=3 μM), and 5 HEPES (pH 7.2). For determination of $Ca^{2+}$-dependence of $K_{Ca}$ channels, cells were dialyzed with pipette solutions containing different $[Ca^{2+}]_{free}$ concentrations and the average current density was calculated for each $[Ca^{2+}]$. The NaCl bath solution contained (mM): 137 NaCl, 4.5 $Na_2HPO_4$, 3 KCl, 1.5 $KH_2PO_4$, 0.4 $MgCl_2$, and 0.7 $CaCl_2$ (pH 7.4).

Detection of apoptosis. Apoptotic nuclei in the neointima Were detected by the terminal transferase-mediated fluorescein-conjugated dUTP nick end labeling (TUNEL) method (Apoptaq® Plus; Qbiogene, Heidelberg, Germany) according to the manufacturer's instructions. Slices Were counterstained with methyl green to visualize all nuclei.

In vitro proliferation studies. To induce growth arrest, A7r5 cells were kept in serum-free medium for 48 h prior to stimulation with EGF (20 ng/ml) or thrombin (1 U/ml) with or without TRAM-34 (1 microM), CLT (1 microM), PD98059 (20 microM), or SB203580 (5 microM). At 5-10% confluence, photomicrographs of cells were taken in a fixed field before and 48 h after stimulation. Cells were counted and the % increase in cell count was calculated for each experiment.

RNA Isolation and quantitative realtime RT-PCR. Cells were harvested at 2 h or 48 h after stimulation by scrapping. RNA was isolated and purified using TRIZOL (Life Technologies, Eggenstein, Germany), following the manufacturer's instructions. RNA (2 μg) was reverse transcribed using random hexamers (Boehringer, Mannheim, Germany) and M-MLV reverse transcriptase (Life Technologies, Eggenstein, Germany) in a 50 μl reaction. Expression was quantified with an ABI Prism 7700 Sequence Detection System (Perkin-Elmer Applied Biosystems Inc). Primers were positioned in the coding region and spanned intronic sequences. Internal oligonucleotides (Biotez, Berlin, Germany) were labeled with 6-carboxy-fluorescein (FAM) on the 5' end and 6-carboxytetramethylrhodamine (TAMRA) on the 3' end. Identity of PCR products was verified by sequencing and linearity of each PCR assay were confirmed by serial dilutions of cDNA. Primer pairs and internal oligonucleotides:

```
rlKCa1:
F 5'-CTGAGAGGCAGGCTGTCAATG-3';( SEQ ID NO: 27)

R ACGTGTTTCTCCGCCTTGTT-3'; (SEQ ID NO: 28)

P 5'-AAGATTGTCTGCTTGTGCACCGGAGTC-3.; (SEQ ID NO:
  29)

rat myosin heavy chain (rMyHC):
F 5'-CATCAATGCCAACCGCAG-3'; (SEQ ID NO: 19)

R 5'-TCCCGAGCATCCATTTCTTC-3'; (SEQ ID NO:20)

P 5'-TGAGGCCATGGGCCGTGAGG-3'; (SEQ ID NO: 30)

rat glyceraldehyde-3-phosphate dehydrogenase
(rGAPDH):
F 5'-CGGCACAGTCAAGGCTGAG-3'; (SEQ ID NO: 31)

R 5'-CAGCATCACCCCATTTGATGT-3'; (SEQ ID NO: 32)

P 5'-CCCATCACCATCTTCCAGGAGCGA-3'. (SEQ ID NO: 33)
```

Each 25 μl PCR reaction consisted of 500 nM forward primer, 500 nM reverse primer, 150 nM probe, 3 μl cDNA, and 1× (final concentration) TaqMan Universal Master Mix (Perkin-Elmer Applied Biosystems Inc). PCR parameters were 50° C.×2 min, 95° C.×10 min, and 50 cycles at 95° C.×15 s, 60° C.×1 min.

The TaqMan® software was employed to calculate a threshold cycle (Ct) which is defined as the cycle at which the reporter fluorescence is distinguishable from the background in the extension phase of the PCR reaction (ABI User Bulletin #2). Real-time RT-PCR signals for rIKCa1 and rMyHC were standardized to rGAPDH by using the equation: $Ct_X - Ct_{rGAPDH} = \Delta Ct$, where $Ct_X$ is the value for the rIKCa1 or the rMyHC probe, and $Ct_{rGAPDH}$ is the value calculated for rGAPDH. The equation, $\Delta Ct_{w/o} - \Delta Ct_X = \Delta\Delta Ct$, was used to determine changes in expression following EGF stimulation, where the experimental $\Delta Ct_X$ value was subtracted from the control $\Delta Ct_{w/o}$ value (w/o=without stimulus) of the same experiment. Fold increases in expression were calculated by the equation, $2^{\Delta\Delta Ct}$=fold change in expression (ABI User Bulletin #2).

In situ cell harvesting and reverse transcription. In situ harvesting of single neointimal VSMC from freshly isolated CA segments, isolation of mature VSMC from healthy CA, reverse transcription of mRNA from single cell samples, and "multiplex" single cell RT-PCR performed. First and 'nested' primer pairs spanning intronic sequences for rSlo, small $K_{ca}$ (rSK1-3), and rIKCa1 were used for the $K_{ca}$ channels. Primers for rMyHC and endothelial nitric oxide synthase (reNOS) served as markers for VSMC and endothelial cells. Identity of PCR products was verified by sequencing. Forward and reverse primer:

```
rlKCa1:
first:
5'-GAGAGGCAGGCTGTCAATG-3';   (SEQ ID NO: 1)

5'-GGGAGTCCTTCCTTCGAGTG-3';  (SEQ ID NO: 24)

nested:
5'-CATCACGTTCCTGACCATTG-3';  (SEQ ID NO: 2)

5'-GTGTTTCTCCGCCTTGTTGA-3';  (SEQ ID NO: 3)

rSlo:
first:
5'-GGACTTAGGGGATGGTGGTT-3';  (SEQ ID NO: 5)

5'-GGGATGGAGTGGACAGAGGA-3';  (SEQ ID NO: 34)

nested:
5'-TTTACCGGCTGAGAGATGCC-3';  (SEQ ID NO: 4)

5'-TGTGAGGAGTGGGAGGAATGA-3'; (SEQ ID NO: 6)

rSK1:
first:
5-GCACACCTACTGTGGGAAGG-3';   (SEQ ID NO: 7)

5'-AGCTCCGACACCACCTCATA-3';  (SEQ ID NO: 8)

nested:
5'-GCTGAGAAACACGTGCACAA-3';  (SEQ ID NO: 9)

5'-TTGGCCTGATCATTCACCTT-3 ;  (SEQ ID NO: 10)

rSK2:
first:
5'-GGAATAATGGGTGCAGGTTG-3';  (SEQ ID NO: 11)

5'-TTTGTTTCCAGGGTGACGAT-3';  (SEQ ID NO: 12)

nested:
5'-CTTGGTGGTAGCCGTAGTGG-3';  (SEQ ID NO: 13)

5'-GAATTTCCGTTGATGCTTCC-3';  (SEQ ID NO: 14)
```

-continued

```
rSK3:
first:
5'-AACCCCTCCAGCTCTTCAGT-3'; (SEQ ID NO: 15)

5'-TGTGGTAGGCGATGATCAAA-3'; (SEQ ID NO: 16)

nested:

5'-GATAACCATGCCCACCAGAC-3'; (SEQ ID NO: 17)

5'-ATTTCAGGGCCAACGAAAAC-3'; (SEQ ID NO: 18)

rMyHC:
first:
5'-CATCAATGCCAACCGCAG-3'; (SEQ ID NO: 19)

5'-TCCCGAGCATCCATTTCTTC-3'; (SEQ ID NO: 20)

nested:
5'-AGGCCACTGAGAGCAATGAG-3'; (SEQ ID NO: 21)

5'-TCAATAACTCTACGGCCTCCA-3'; (SEQ ID NO: 22)

reNOS:
first:
5'-GAGAGGCAGGCTGTCAATG-3'; (SEQ ID NO: 23)

5'-GGGAGTCCTTCCTTCGAGTG-3'; (SEQ ID NO: 24)

nested:
5'-CCAGCTCTGTCCTCAGAAGG-3'; (SEQ ID NO: 25)

5'-ATGGATGAGCCAACTCAAGG-3'. (SEQ ID NO: 26)
```

GenBank™ accession numbers: rIKCa1: AF156554; rSlo: AF135265; rSK1: AF000973; rSK2: U69882; rSK3: U69884; rMyHC: X16262; reNOS: AJ011116; rGAPDH: AB017801.

Statistical analysis. Data are given as mean±SE. If appropriate, the Wilcoxon Rank-Sum test or $\chi$-square analyses were used to assess differences between groups. P-values of $P<0.05$ were considered significant.

Results

Alterations in $K_{Ca}$ functional expression in neointimal VSMC following BCI. To measure functional $K_{Ca}$ channel expression, Applicants performed whole-cell patch-clamp experiments in combination with 'single-cell' RT-PCR analysis on neointimal VSMC in situ and on freshly isolated mature VSMC. Mature VSMC (n=14) from normal CA exhibited an outward $Ca^{2+}$-activated and voltage-dependent $K^+$ current with characteristics of the cloned $BK_{Ca}$ channel. The outward $K^+$ current was small at negative membrane potentials, increased steeply at depolarizing positive membrane potentials, and was blocked by the selective $BK_{Ca}$ inhibitor, IbTX (FIG. 1a, left panel), with a potency similar to the cloned $BK_{Ca}$ channel ($K_D$ 11±3 nM, FIG. 1a, left inset). The selective $SK_{Ca}$ blocker apamin (APA, 1 µM), and the $IK_{Ca}$ blockers TRAM-34 (1 µM) and CLT (1 µM) had no effect on this current (data not shown). The $BK_{Ca}$ opener NS1619 stimulated the current, whereas 1-EBIO, an opener of $IK_{Ca}$ and $SK_{Ca}$, had no detectable effect (not shown). A small residual voltage-gated $Ca^{2+}$-independent ($K_v$) $K^+$ current (1.1±0.2 pA/pF at 0 mV) in these cells was sensitive to 2 mM 4-aminopyridine (FIG. 1a, right panel).

Two weeks after BCI, neointimal VSMC (n=30) exhibited a substantially altered $K^+$ current pattern. In a majority of neointimal VSMC (19 of 30), two calcium-activated $K^+$ currents were seen (FIG. 1b, top left panel) with properties resembling $BK_{Ca}$ and $IK_{Ca}$ channels. The $IK_{Ca}$ component seen at negative potentials was eliminated by the selective $IK_{Ca}$-inhibitor TRAM-34, leaving a residual $BK_{Ca}$ current that increased steeply at positive potentials. A combination of TRAM-34 and IbTX completely suppressed both components (FIG. 1b, top left panel). In 11 of 30 of these neointimal VSMC, $BK_{Ca}$ currents were absent, and these cells contained only $IK_{Ca}$ currents (FIG. 1b top right panel and both bottom panels). These currents were half-maximally activated by ~350 nM $[Ca^{2+}]_i$ (FIG. 1b bottom left panel), and were blocked by TRAM-34 ($K_D$ 10±2 nM), CLT ($K_D$ 31±4 nM) and charybdotoxin (ChTX; $K_D$ 5±1 nM) (FIG. 1b bottom right panel) with potencies similar to the cloned channel (18), but not by 1 µM of the SK inhibitor APA or 2 mM 4-aminopyridine (not shown). The $IK_{Ca}$ opener 1-EBIO (100 µM, n=7, not shown) increased the amplitude of the current by 202±29%. These properties of the $IK_{Ca}$ current in neointimal VSMC are remarkably similar to the cloned IKCa1 channel, and the native $IK_{Ca}$ channel in human and rat endothelial cells, proliferating rat aortic VSMC, human lymphocytes, human pancreas, fibroblast cell lines. These results demonstrate a significant shift from predominantly $BK_{Ca}$ functional expression in mature VSMC to a mixture of $IK_{Ca}$ and $BK_{Ca}$ in neointimal cells two weeks post BCI.

Alterations in $BK_{Ca}$ and IKCa1 mRNA expression in neointimal VSMC following BCI correlate with changes in functional expression. Applicants used 'multiplex' single-cell RT-PCR to determine whether the changes in functional $BK_{Ca}$ and $IK_{Ca}$ expression following BCI were correlated with alterations in mRNA levels for the rSlo and IKCa1 genes, respectively. The VSMC marker rMyHC was detected in all mature VSMC (34/34), in all neointimal VSMC (18/18) two Weeks post BCI, and in 63% (19/30) of neointimal VSMC six weeks after BCI. Endothelial cell-specific eNOS expression was not detected in any of the cell samples, demonstrating that the VSMC samples were not contaminated with endothelial cells. None of the negative controls (n=24) yielded any PCR products.

Figure 1B:
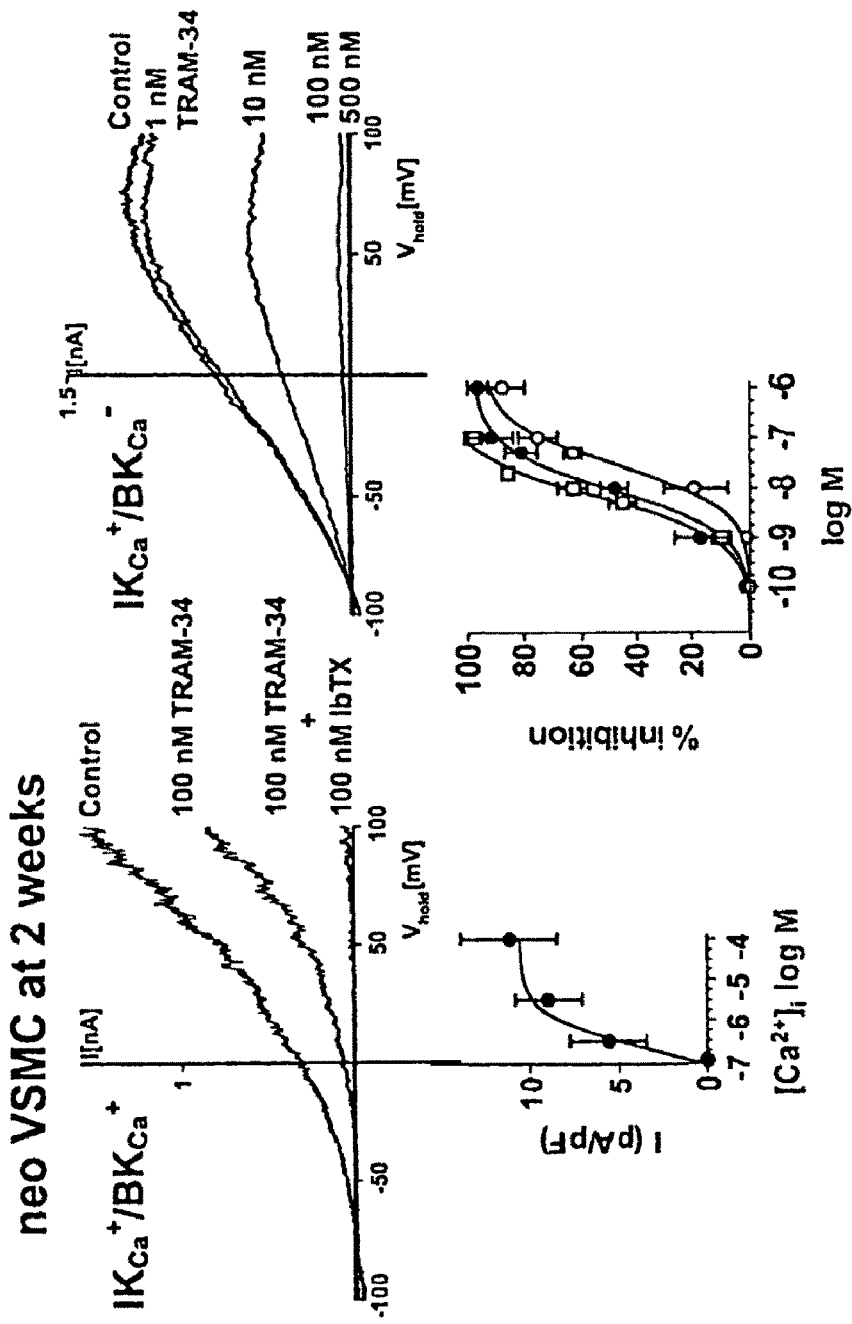
FIG. 1b is a set of graphs showing mixed $BK_{Ca}$ and $IK_{Ca}$ currents in neointimal VSMC at two weeks after BCI and blockade of $IK_{Ca}$ currents by TRAM-34 and $BK_{Ca}$ currents by IbTX (left upper panel); concentration-dependent blockade of $IK_{Ca}$-currents by TRAM-34 in cell expression pure IKCa1 current (right upper panel); $Ca^{2+}$-dependence of $IK_{Ca}$-currents (left lower panel); and pharmacology of $IK_{Ca}$-currents for TRAM-34 (n=6-7; ●), CLT (n=3-5; ○), and ChTX (n=34; □), respectively (right lower panel).
Figure 2B:
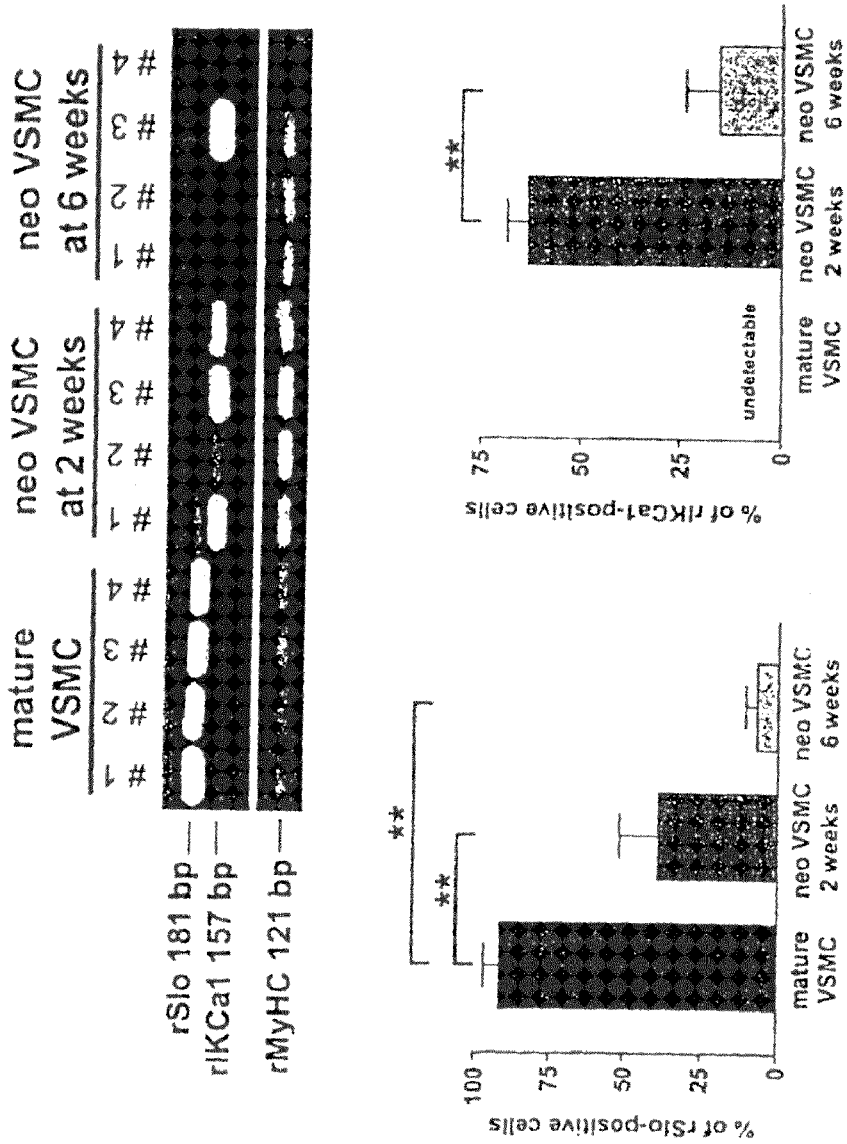
FIG. 2b shows a representative expression pattern of the $K_{Ca}$ genes rSlo and rIKCa1 (upper panel) and rMyHC (lower panel) in mature VSMC and neointimal VSMC at two and six weeks after BCI. The columns at the bottom of the figure show the results of quantitative analysis of rSlo and rIKCa1 expression in mature VSMC (rats, n=9) and neointimal VSMC at two weeks (rats, n=5) and six weeks (rats, n=6). Values are given as mean±SE; **P<0.01, Wilcoxon Rank-Sum test.

Consistent with the electrophysiology data in FIG. 1, mature VSMC that express $BK_{Ca}$ and not $IK_{Ca}$ channels contained substantial quantities of rSlo mRNA (87%; 54/62) and no rIKCa1 mRNA (0/27; FIGS. 2a and b). Transcripts of the related SK1-SK3 genes Were also not detected in these cells (FIG. 2a). Two weeks following BCI, the $K_{Ca}$ gene expression pattern in neointimal VSMC was altered (FIGS. 2a and b) in keeping with the changes observed in the amplitude of $BK_{Ca}$ and $IK_{Ca}$ currents in these cells (FIG. 1). Applicants detected rSlo transcripts significantly less frequently in these cells (24/67; 36%) compared to mature VSMC (P<0.01, $\chi$-square analysis), whereas rIKCa1 transcripts Were more frequently detected (42/67; 63%; P<0.001). Interestingly, a faint rSK3 band is detected in these neointimal VSMC (FIG. 2a), although the contribution of SK3 to the $K_{Ca}$ current must be small because it was insensitive to 1 µM APA and a combination of TRAM-34 and IbTX completely suppressed the current (FIG. 1a, left). Corroborating the decreased functional expression of $BK_{Ca}$ and $IK_{Ca}$ currents in VSMC six weeks post BCI, rSlo was detectable in only 6% (4/69) of these samples and rIKCa1 in only 16% (11/69). These results indicate that changes in Slo and IKCa1 mRNA levels following BCI contribute to the observed changes in $BK_{Ca}$ and $IK_{Ca}$ functional expression in VSMC.

EGF-induced up-regulation of IKCa1 expression and proliferation of rat VSMC via MEK activation. Activation of the Ras/Raf/MEK/ERK-signaling system has been shown to up-regulate $IK_{Ca}$ expression and thus affect proliferation of rat fibroblast in vitro. $IK_{Ca}$ up-regulation in VSMC following BCI might therefore be mediated by activation of this signaling pathway. To test this hypothesis, Applicants compared $IK_{Ca}$ function and rIKCa1 expression in the aortic VSMC cell line A7r5 before and 48 hours after stimulation with the mitogenic factor EGF. Following stimulation, the amplitude of the $IK_{Ca}$ current increased threefold compared to untreated cells (FIG. 3a, left panel; P<0.01). Both treated and untreated A7r5 cells were devoid of substantial $BK_{Ca}$ or voltage-gated $K^+$ currents. The $IK_{Ca}$ current was activated by $Ca^{2+}$ with an $EC_{50}$ of ~350 nM and was blocked by TRAM-34 ($K_D$ 10±1 nM, not shown) with a potency similar to IKCa1. Involvement of the MEK/ERK pathway in EGF-induced $IK_{Ca}$ up-regulation was demonstrated with the MEK-inhibitor PD98059. Pretreatment with PD98059 (20 µM) for 30 min prior to EGF stimulation prevented the increase in $IK_{Ca}$ current amplitude (FIG. 3a), similar to the FGF effect in fibroblasts. Parallel RT-PCR studies revealed a 3-fold increase in rIKCa1 transcript levels 48 hours following EGF stimulation, which was blocked by PD98059, but not by the p38-MAP kinase inhibitor SB203580 (FIG. 3a, right panel); a 6-fold increase in IKCa1 mRNA levels was detected as early as 2 hours after EGF stimulation, as shown in Table 8 below. In contrast, thrombin (1 U/ml) was ineffective in augmenting $IK_{Ca}$ current amplitude or in up-regulating expression of rIKCa1 transcripts. Taken together, these results show that EGF-stimulated A7r5 cells resemble proliferating neointima in vivo, suggesting that EGF-induced activation may contribute to the increased $IK_{Ca}$ expression seen in neointimal VSMC two Weeks post BCI.

cells. EGF significantly induced mitogenesis of these cells, which was significantly greater than that observed in unstimulated or thrombin-stimulated cells (FIG. 3c). TRAM-34 and CLT suppressed mitogenesis to the levels seen in unstimulated cells (FIG. 3c). The MEK-inhibitor PD98059 completely suppressed EGF-induced mitogenesis, while the p38-MAP kinase inhibitor SB203580 had no effect (FIG. 3c). These results suggest that the $IK_{Ca}$ channel plays a role in neointimal proliferation as it has been reported to do in lymphocytes and fibroblasts.

TRAM-34 and CLT suppress BCI-induced intimal hyperplasia in vivo. Based on the up-regulation of $IK_{Ca}$ channel expression in VSMC following BCI and the effectiveness of

TABLE 8

Mitogenic Regulation of rIKCa1 Expression and $IK_{Ca}$ Function in Rat Aortic VSMC (A7r5)

| Cell Treatment | n | GAPDH (Ct) | rIK1 (ΔCt) | rIK1 (ΔΔCt) (x-fold Increase) | rMyHC (ΔCt) | Cell Treatment | n (Cells) | $I_{rIK1}$ (pA/pF) |
|---|---|---|---|---|---|---|---|---|
| w/o | 16 | 22.6 ± 0.5 | 12.4 ± 0.4 | | 9.2 ± 0.3 | w/o | 14 | 0.8 ± 0.2 |
| EGF (2 h) | 17 | 22.7 ± 0.6 | 9.6 ± 0.4*** | 2.8 (~6-fold) | | EGF | 16 | 3.4 ± 0.6*** |
| EGF (48 h) | 11 | 21.7 ± 0.8 | 10.8 ± 0.4** | 1.6 (~3-fold) | 9.0 ± 0.4 | EGF + PD98059 | 23 | 1.0 ± 0.2# |
| EGF + PD98059 (2 h) | 2 | 22.9 ± 3.7 | 13.2 ± 0.2 | −0.8 | | EGF + SB203580 | 7 | 2.2 ± 0.5** |
| EGF + PD98059 (48 h) | 4 | 22.7 ± 0.4 | 12.6 ± 0.6# | −0.2 | 9.4 ± 0.4 | | | |
| EGF + SB203580 (48 h) | 5 | 19.1 ± 1.7 | 10.7 ± 0.4* | 1.7 (3-fold) | 9.6 ± 0.2 | Thrombin | 11 | 0.4 ± 0.1 |
| Thrombin (48 h) | 2 | 23.8 ± 0.5 | 12.2 ± 0.9 | 0.2 | | | | |

Real-time RT-PCR analysis of rIKCa1 and rMyHC expression (left) and whole cell currents of $IK_{Ca}$ at 0 mV (right) in A7r5 cells following EGF stimulation for 48 h. Values are given as mean ± SE; $Ct_x - Ct_{rGAPDH} = \Delta Ct$; $\Delta Ct_{w/o} - \Delta Ct_x = \Delta\Delta Ct$; $2^{\Delta\Delta Ct}$ = fold increase in expression, e.g. 1 ΔΔCt = 2-fold; 2 ΔΔCt = 4-fold;
*P < 0.05,
**P < 0.01,
***P < 0.001 vs. w/o;
P < 0.05,
P < 0.01, vs. EGF-stimulated cells; Wilcoxon Rank-Sum test.

To test whether the enhanced $IK_{Ca}$ expression in VSMC might have functional consequences, Applicants examined whether the IKCa1 inhibitors TRAM-34 (1 µM) and CLT (1 µM) could suppress EGF-stimulated mitogenesis of A7r5 cells, Applicants examined whether $IK_{Ca}$ blockade might reduce intimal hyperplasia in the carotid arteries of rats following BCI. The data are summarized in Table 9 below.

TABLE 9

Effect of TRAM-34 and CLT on intimal hyperplasia after BCI

| Treatment group | n | Neointimal Area (mm²) | Medial Area (mm²) | N/M | Residual Lumen Area (mm²) | rL/cL | Nuclei Count (Cell No.) | Rate of Apoptosis (%) | Collagen Content (%) |
|---|---|---|---|---|---|---|---|---|---|
| Vehicle | | | | | | | | | |
| 1 week | 4 | 0.011 ± 0.010 | 0.084 ± 0.005 | 0.13 ± 0.01 | 0.22 ± 0.01 | 0.93 ± 0.04 | 159 ± 17 | | |
| 2 weeks | 11 | 0.097 ± 0.006 | 0.099 ± 0.003 | 1.05 ± 0.06 | 0.16 ± 0.01 | 0.64 ± 0.05 | 984 ± 82 | 0.9 ± 0.6 | 11 ± 2 |
| 6 weeks after BCI | 5 | 0.169 ± 0.008 | 0.091 ± 0.008 | 1.92 ± 0.22 | 0.13 ± 0.01 | 0.50 ± 0.02 | 1525 ± 79 | <<1 | 19 ± 3 |
| TRAM-34 | | | | | | | | | |
| 1 week | 4 | 0.004 ± 0.001* | 0.084 ± 0.004 | 0.05 ± 0.01** | 0.21 ± 0.02 | 0.96 ± 0.05 | 47 ± 16* | | |
| 2 weeks | 6 | 0.063 ± 0.005** | 0.095 ± 0.002 | 0.66 ± 0.05** | 0.21 ± 0.02* | 0.91 ± 0.06** | 601 ± 36** | 1.0 ± 0.6 | 15 ± 2 |
| 6 weeks after BCI | 5 | 0.096 ± 0.018** | 0.082 ± 0.006 | 1.15 ± 0.18** | 0.18 ± 0.01** | 0.81 ± 0.06** | 612 ± 97*** | <<1 | 11 ± 4 |

TABLE 9-continued

Effect of TRAM-34 and CLT on intimal hyperplasia after BCI

| Treatment group | n | Neointimal Area (mm$^2$) | Medial Area (mm$^2$) | N/M | Residual Lumen Area (mm$^2$) | rL/cL | Nuclei Count (Cell No.) | Rate of Apoptosis (%) | Collagen Content (%) |
|---|---|---|---|---|---|---|---|---|---|
| CLT | | | | | | | | | |
| 2 weeks after BCI | 7 | 0.049 ± 0.010*** | 0.102 ± 0.004 | 0.49 ± 0.10*** | 0.24 ± 0.02** | 0.82 ± 0.05* | 407 ± 82*** | 0.6 ± 0.5 | 13 ± 1 |

N/M = ratio of neointimal/medial areas; rL/cL = residual Lumen/contralateral Lumen; Values are given as mean ± SE;
*P < 0.05,
**P < 0.01,
***P < 0.001 vs. vehicle, Wilcoxon Rank-Sum test.

An initial trial with CLT (120 mg/kg/d administered subcutaneous) for two weeks provided encouraging results, but the CLT-treated rats gained significantly less Weight than the vehicle-treated group and developed hepatomegaly due to CLT's reported liver toxicity mediated via inhibition of P450-dependent enzymes. Applicants therefore switched to the more selective $IK_{Ca}$ inhibitor TRAM-34 (120 mg/kg/d, subcutaneous), which has no effect on P450-dependent enzymes and should therefore not be liver toxic. In the vehicle-treated group neointima formation progressively increased from Week-1 to Week-6 post-BCI. Applicants observed a progression of neointima formation in the TRAM-34-treated group, but the area of the neointimal-cell layer in these rats was significantly smaller than vehicle-treated rats at Week-1 (−64%; P<0.01), Week-2 (−35%; P<0.01), and Week-6 (−43%; P<0.01) post BCI (Table 9). Two weeks treatment with CLT also resulted in a pronounced reduction of neointimal formation (−50%; P<0.001, Table 9). The area of the medial smooth-muscle-cell layer was not different between rats treated with TRAM-34, CLT, or vehicle. The ratio of neointimal/medial areas (N/M) in TRAM-34- and CLT-treated rats was therefore significantly smaller than that of the respective vehicle-treated groups at all times measured post-BCI. The reduced neointima formation in TRAM-34-treated animals resulted in significantly larger residual lumina at two weeks (+34%; P<0.05) and at six Weeks (+44%; P<0.01) after BCI compared to vehicle-treated rats. Due to the low amount of neointima formation at Week-1 post-BCI, there was no statistical difference in lumen area of TRAM-34-treated rats and vehicle-controls. CLT-treated animals also displayed larger residual lumina at two Weeks (+49%; P<0.001) after BCI. Applicants normalized the lumen area of the injured CA (rL) to that of the uninjured contralateral CA (rL/cL). Table 9 shows that TRAM-34-treated rats displayed a lower degree of lumen narrowing (higher rL/CL values) at Week-2 (−9%; P<0.01) and Week-6 (−19%; P<0.01) compared to vehicle-treated controls (−36% at Week-2 and −50% Week-6). A lower degree of lumen narrowing was also observed in the CLT-treated group at two weeks after BCI (−18%; P<0.05).

TRAM-34 treatment caused no visible side effects or organ damage as determined macroscopically during the course of the study. After transient weight loss in the first week due to surgery, TRAM-34-treated rats gained weight (30±5 g after two weeks; 99±6 g after six weeks) similar to the vehicle-treated group (25±4 g after two weeks, 90±15 g after six weeks). In contrast, the CLT-treated group gained significantly less weight (7±6 g; P<0.05) within two weeks after BCI. Subcutaneous injections of TRAM-34 and CLT resulted in serum levels of 102±21 nM and 375±75 nM, respectively, as determined with a bioassay at the end of the treatment and 24 h after the last injection.

To understand the mechanism by which TRAM-34 and CLT reduced neointima formation, Applicants investigated cell proliferation, apoptosis, and extracellular matrix (collagen) content. The neointimal nuclei count, a measure of cell proliferation, was reduced by −70% (P<0.05) after one week, by −39% (P<0.01) after two weeks, and by −61% (P<0.001) after six weeks of TRAM-34-treatment compared to vehicle-treated rats. A similar reduction (−59%, P<0.001) in neointimal nuclei count was observed in the CLT-treated group at two weeks after BCI. However, the collagen content and the rate of apoptosis (percentage of apoptotic nuclei) in the neointima was not different in TRAM-34- and CLT-treated rats compared to vehicle-treated controls. Taken together Applicants' results demonstrate that $IK_{Ca}$ blockers reduce neoimtima formation by inhibition of VSMC proliferation.

Percutaneous balloon angioplasty, a procedure used to relieve arterial stenosis and improve blood flow, is frequently complicated by vascular restenosis due to proliferation of VSMC. Using a balloon catheter injury model to the rat carotid artery, Applicants demonstrate that neointimal formation following angioplasty is associated with an alteration in $K_{Ca}$ channel expression in VSMC. Mature VSMC exclusively expressed $BK_{Ca}$, whereas proliferating neointimal cells down-regulated $BK_{Ca}$ and up-regulated IKCa1. Blockade of IKCa1 inhibited EGF-induced proliferation of VSMC in vitro and reduced neointimal formation in vivo post-BCI. IKCa1 blockade might therefore represent a novel therapeutic strategy for the prevention of restenosis following angioplasty.

Neointimal proliferation and IKCa1 up-regulation following BCI is mediated by numerous mitogenic factors. Using the aortic VSMC cell line A7r5 as a model system Applicants demonstrated that EGF augmented IKCa1 RNA and functional expression, and induced proliferation, via activation of the MEK/ERK signaling pathway. IKCa1 has been similarly reported to be up-regulated and to contribute to the proliferation of growth factor-stimulated fibroblasts and mitogen-activated human T lymphocytes. In fibroblasts, like VSMC, IKCa1 up-regulation is mediated through the Ras/Raf/MEK/ERK signaling cascade, and in T-lymphocytes augmentation of IKCa1 levels occurs as a result of AP1-dependent transcription. Thrombin, another putative mitogen for VSMC, failed to up-regulate IKCa1 expression or induce mitogenesis, possibly because it acts more as a stimulus for differentiation rather than as a mitogenic factor in VSMC. Enhanced IKCa1 expression may therefore be a functional characteristic of proliferating and de-differentiated cells.

IKCa1 might promote VSMC mitogenesis by enhancing the electrochemical driving force for $Ca^{2+}$ influx via membrane hyperpolarization and thus sustain a high intracellular $Ca^{2+}$ concentration, as has been reported in lymphocytes and fibroblasts. IKCa1 may play a more important role than $BK_{Ca}$ in regulating the membrane potential and calcium signaling of proliferating VSMC because its higher $Ca^{2+}$ affinity would result in IKCa1 channel opening and membrane hyperpolarization in response to subtle increases in the intracellular $Ca^{2+}$ concentration. Induction of IKCa1 expression might thus be an essential step in promoting neointimal VSMC proliferation following BCI. Consistent with such a role, IKCa1 blockade by CLT, ChTX and the specific inhibitor TRAM-34 suppressed the proliferation of cultured VSMC. IKCa1 blockers may therefore have therapeutic value for preventing neointimal proliferation and restenosis following BCI.

In a rat model of BCI, administration of CLT significantly reduced neointimal thickening, but the trial was discontinued after two weeks due to the development of severe hepatomegaly and reduced weight gain, presumably because of liver toxicity caused by blockade of cytochrome P450-dependent enzymes. A subsequent trial with TRAM-34, an IKCa1 selective inhibitor that does not block cytochrome P450 enzymes, significantly reduced neointimal hyperplasia without causing visible signs of organ damage or gastrointestinal side-effects. TRAM-34's therapeutic effect was due to inhibition of neointimal cell proliferation and not due to increased apoptosis or decreased matrix formation. In conclusion, targeting IKCa1 channels in proliferating VSMC with TRAM-34 might have therapeutic utility in the prevention of restenosis after angioplasty, and for the treatment of other cardiovascular disorders characterized by abnormal VSMC proliferation.

Although the compounds of Example 22 were delivered to the test subjects subcutaneously, other routes or modes of administration are included within the scope of this invention. Suitable routes of administration include, but are not limited to, inhalation, transdermal, oral, rectal, transmucosal, intestinal and parenteral administration, including intramuscular, subcutaneous and intravenous injections. and through implantable drug delivery devices such as coated stents or stent-grafts. The compounds described herein, or pharmaceutically acceptable salts or hydrates thereof, may be administered singly or in combination with other therapeutic agents, e.g. analgesics, antibiotics and other immunosuppressive drugs like cyclosporin A or Kv1.3 selective blockers. The active compound (T34) may be administered per se or in the form of a pharmaceutical composition wherein the active compound is in admixture with one or more physiologically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent on the route of administration chosen. For parenteral administration (bolus injection or continuous infusion), the agents of the invention may be formulated in water soluble form in aqueous solutions, preferably in physiologically compatible buffers such as Hank's solution, Ringer's solution, or physiological saline buffer. Additionally, suspensions of the compounds may be prepared as oily injections with fatty oils, synthetic fatty acid esters, or liposomes. The compounds may also be formulated as a depot preparation. For oral administration, the compounds can be formulated readily by combining the active compound with pharmaceutically acceptable carriers Well known in the art. Such carriers enable the compounds of the invention to be formulated as tablets, pills, dragees, capsules, liquids, gels, syrups, slurries, suspensions an the like, for oral ingestion for patients to be treated. Suitable excipients are, in particular, fillers such as sugars, including lactose, sucrose, mannitol, or sorbitol: cellulose preparations such as, for example maize starch, wheat starch, rice starch, potato starch, gelatin, gum tragacanth, methyl cellulose, hydroxypropylmethylcellulose, sodium carboxymethylcellulose, and/or polyvinylpyrrolidone.

Example 23

Implantable Stent which Elutes Compound(s) of the Present Invention

FIG. 4 shows a general example of a drug-eluting stent 10 of the present invention positioned within a diseased artery A of a human or veterinary patient. Stents 10 of this invention may be coated with or may otherwise contain or include one or more compounds of Formula I or IA above, alone or in combination with other drugs or therapeutic agents such as rapamycin (Sirolimus) and/or paclitaxel (Taxol). In this particular example, the stent 10 is coated with 1-[(2-chlorophenyl)diphenyl methyl]-1H-pyrazole (designated as TRAM-34) such that a proliferation-inhibiting does of TRAM 34 is delivered to the wall of the artery A adjacent to the stent 10, thereby inhibiting restenosis within or near the stent 10.

As those of skill in the art will appreciate, the therapeutic compound(s) may be coated on or included with the stent 10 using any suitable technology. For example, the stent 10 may be dip coated with a solution of TRAM 34. Or, the TRAM 34 may be combined with a polymeric delivery matrix and the TRAM-34/polymer matric combination may be applied to the stent 10 by dipping, painting or any other suitable deposition technique.

Also, although this example shows a stent 10 of a simple zig-zag design, it will be appreciated that the compounds of the present invention may be coated or or otherwise included with stents of any type or design including self-expanding stents or stent-grafts, balloon-expandable stents or stent-grafts, multicellular or mesh stents or stent-grafts, helical stents or stent grafts, roll-up stents or stent grafts, etc.

While this invention has been described with respect to various specific examples and embodiments, it is to be understood that the invention is not limited thereto and that it can be variously practiced with the scope of the following claims.

APPENDIX A

Exemplary Compounds

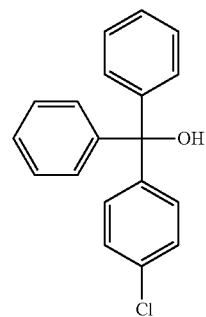

T1

-continued
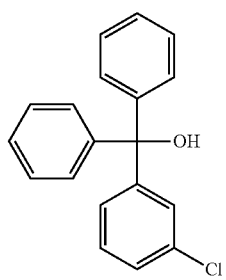 T2
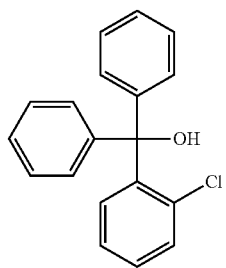 T3
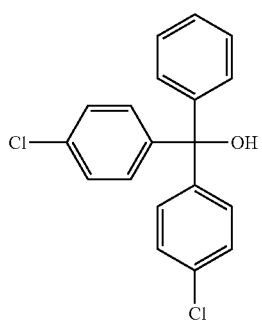 T4
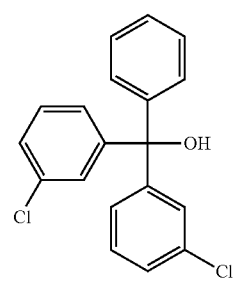 T5
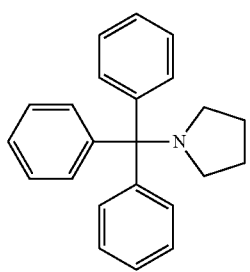 T7
-continued
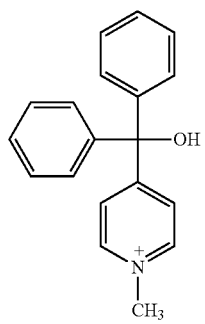 T8
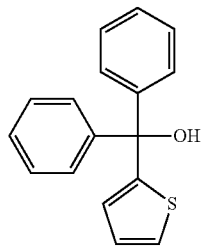 T9
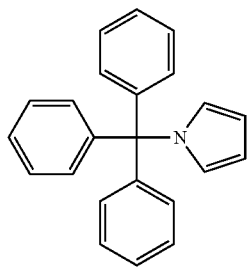 T10
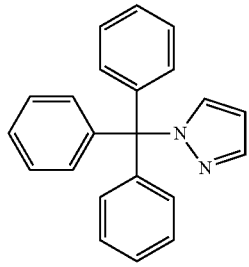 T11
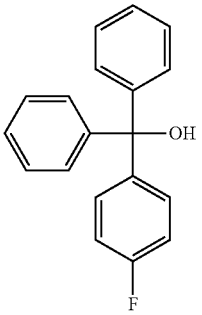 T12

T13 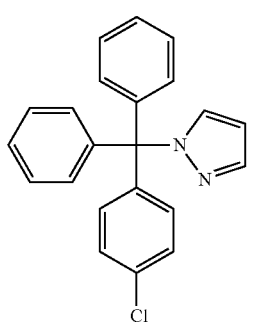
T14 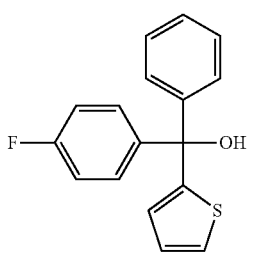
T15 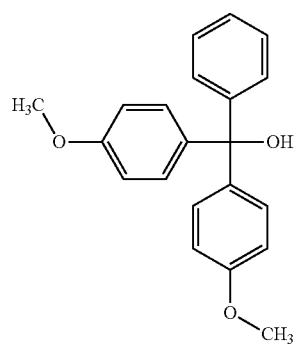
T16 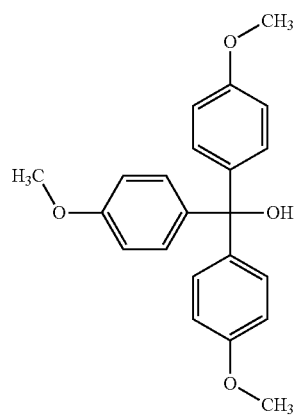
T17 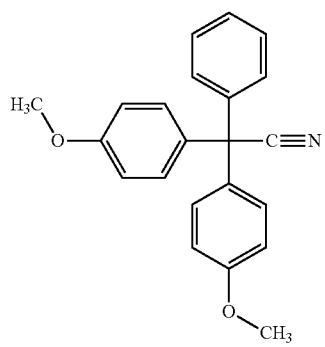
T18 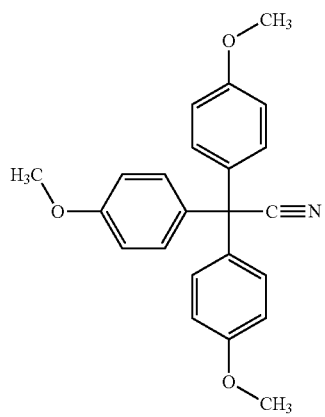
T19 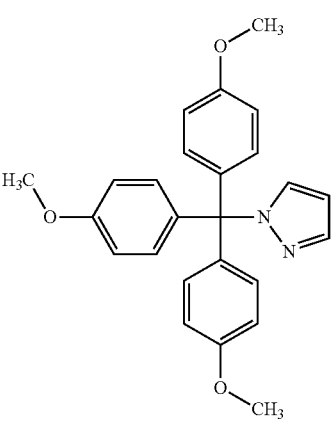

T20
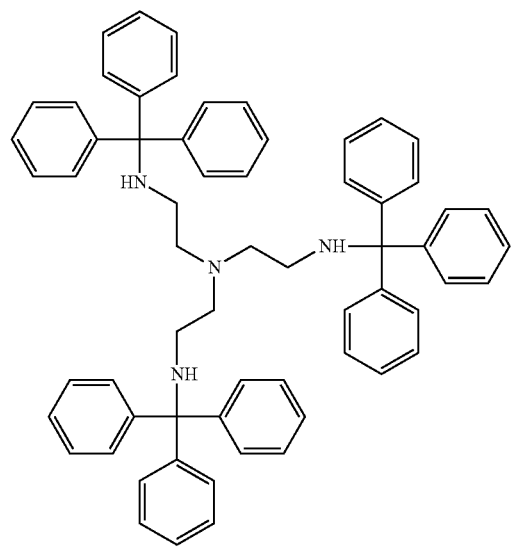
T21
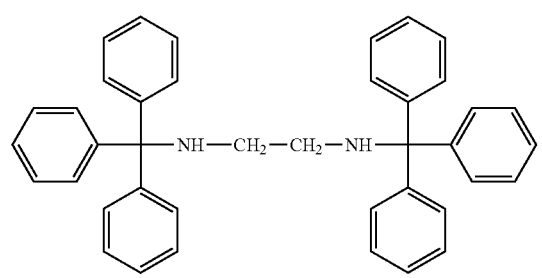
T22
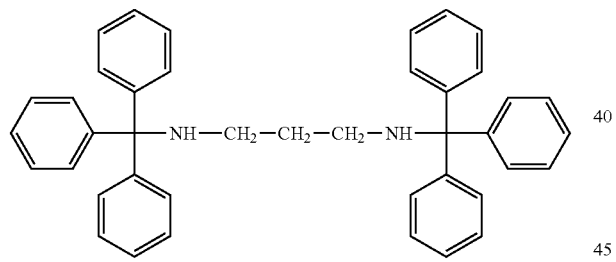
T23
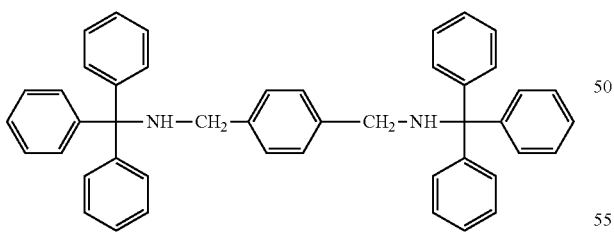
T24
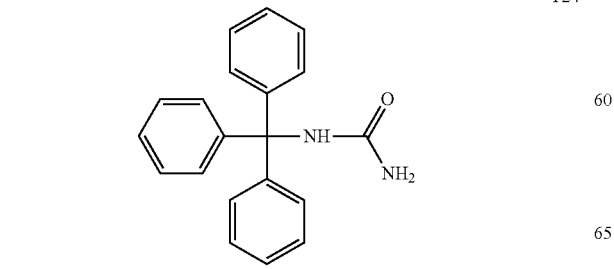
T26
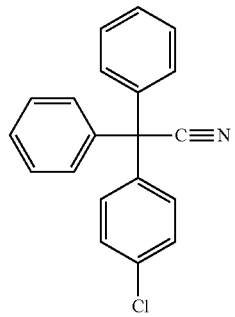
T27
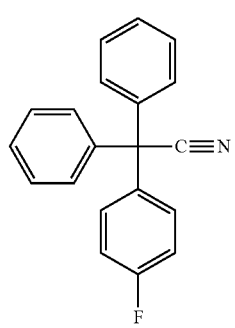
T28
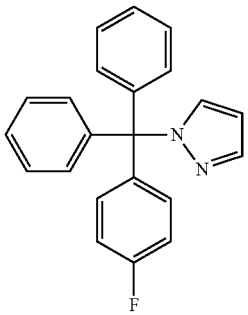
T29
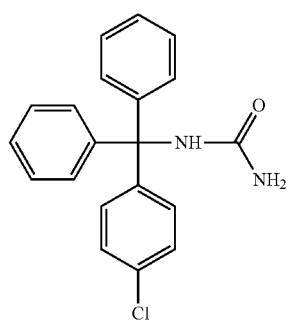
T30
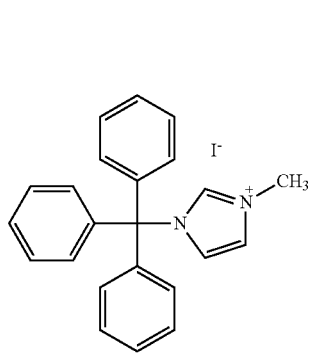

| | |
|---|---|
| T31 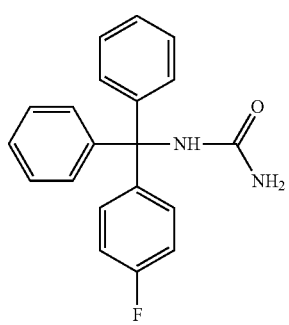 | T37 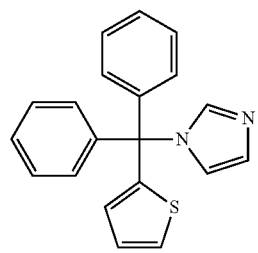 |
| T32 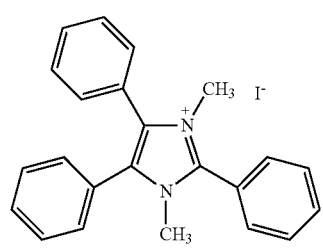 | T38 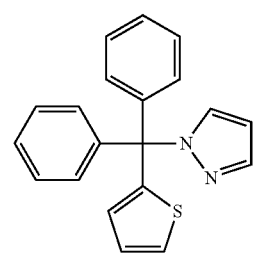 |
| T33 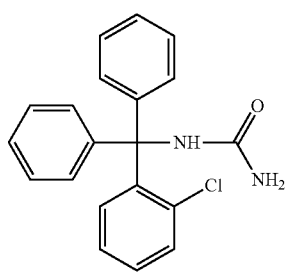 | T39 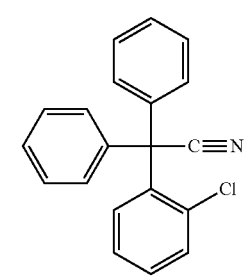 |
| T34 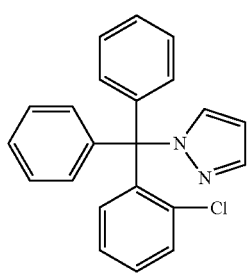 | T40 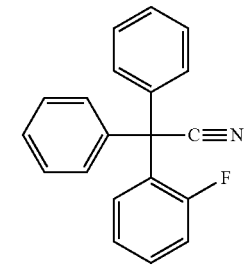 |
| T35 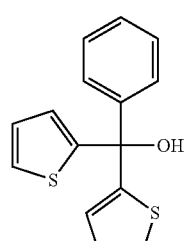 | T41 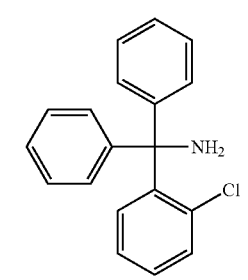 |
| T36 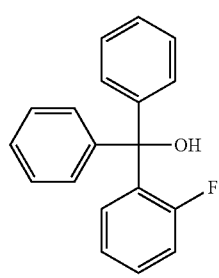 | |

T42
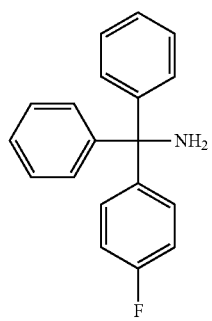
T43
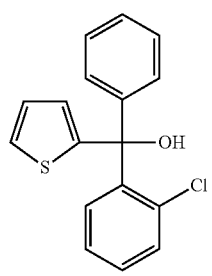
T44
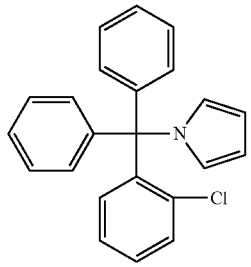
T45
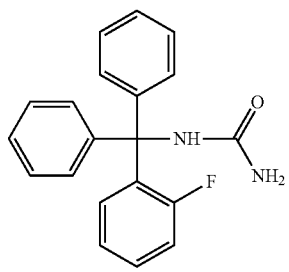
T46
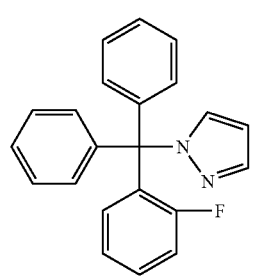
T47
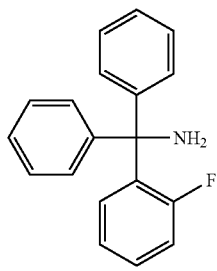
T48
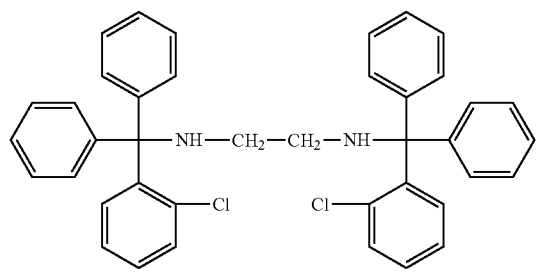
T49
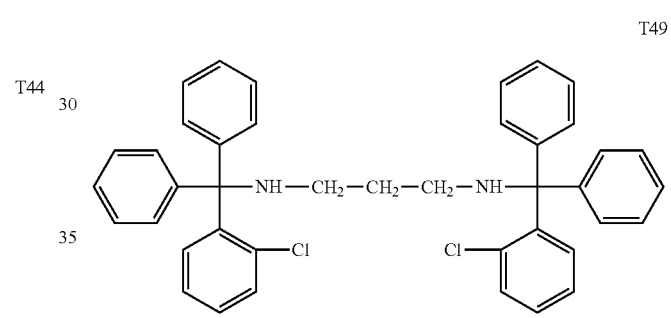
T50
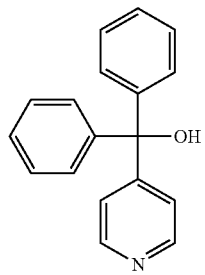
T51
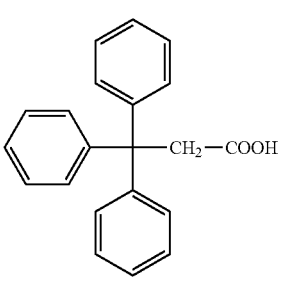

-continued
T52 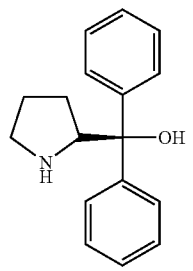
T53 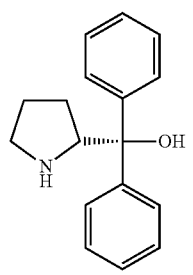
T54 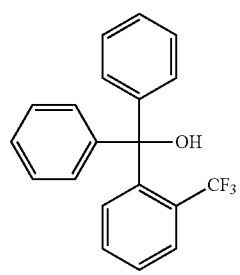
T55 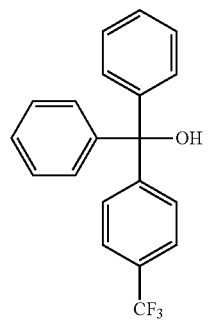
T56 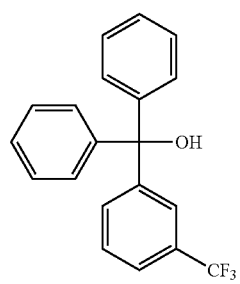
-continued
T57 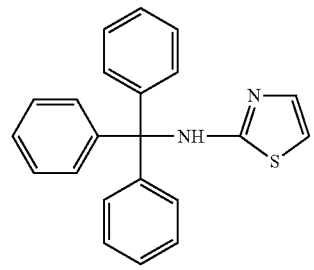
T58 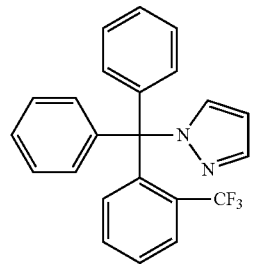
T59 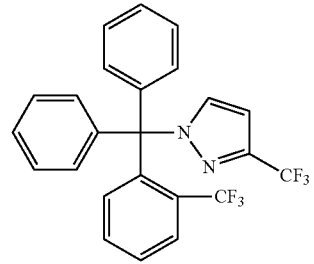
T60 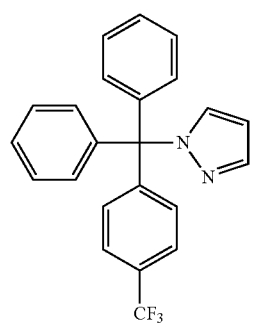
T61 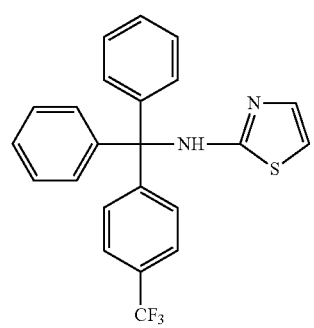

T62
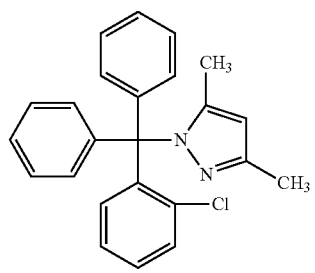
T63
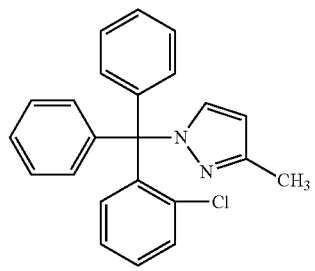
T64
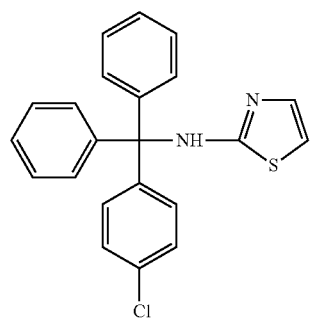
T65
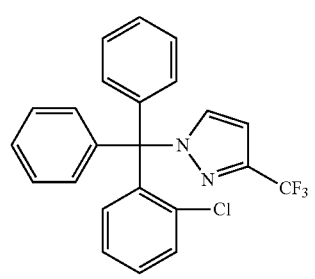
T66
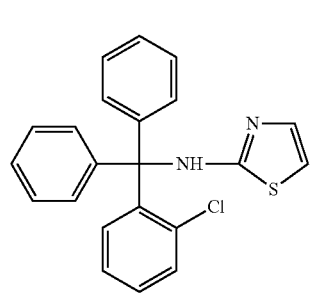
T67
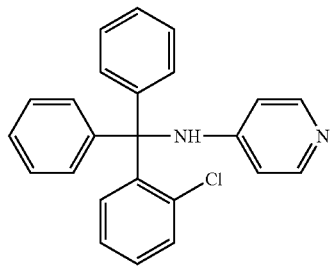
T68
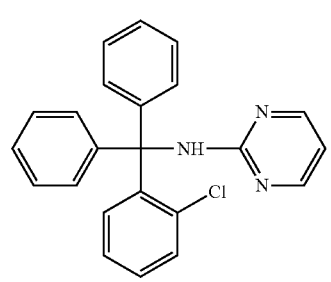
T69
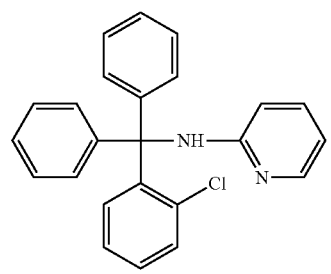
T70
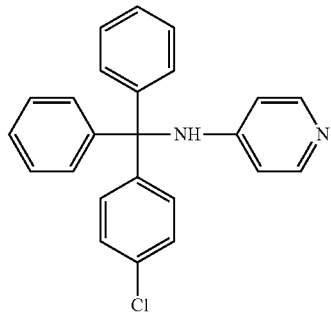
T71
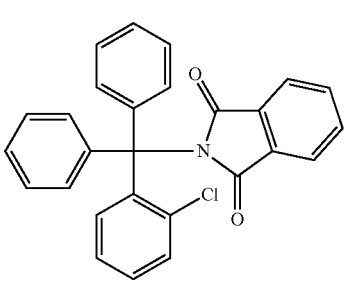

T72 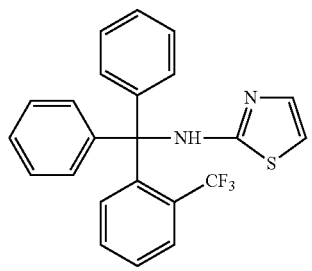
T73 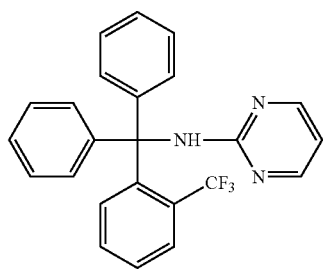
T74 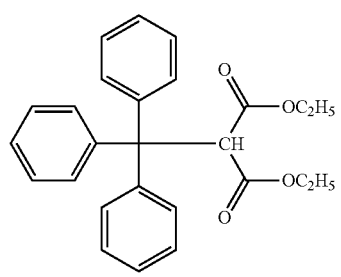
T75 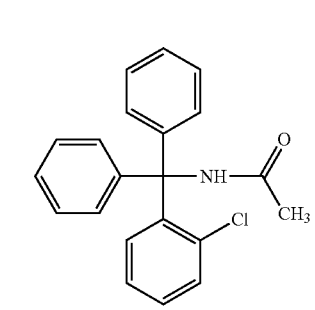
T76 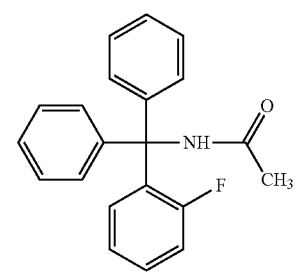
T77 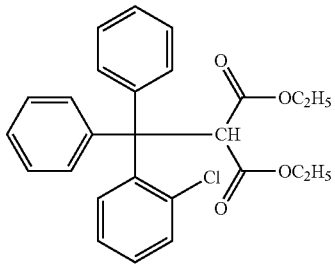
T78 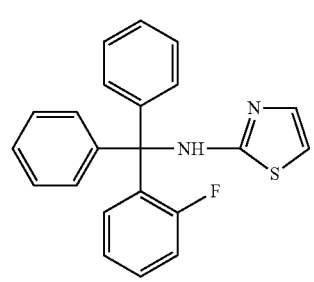
T79 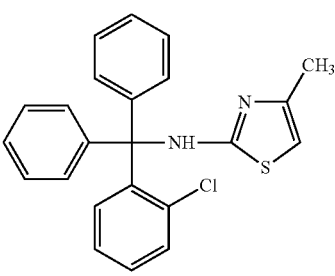
T81 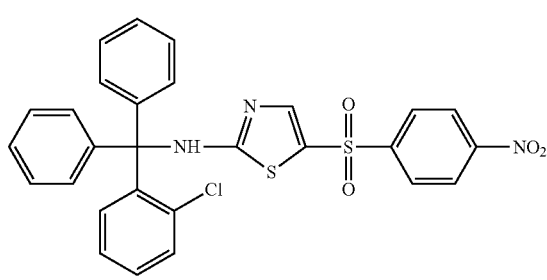
T82 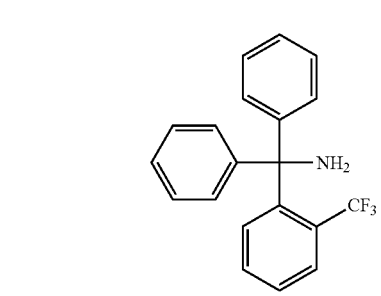

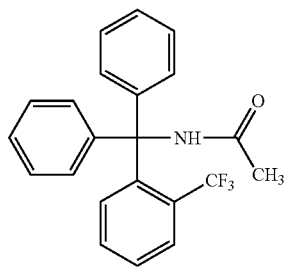

T83

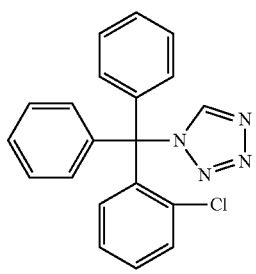

T84

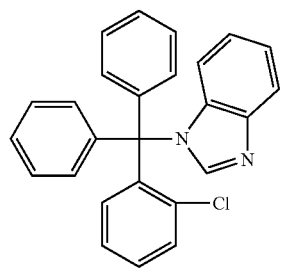

T85

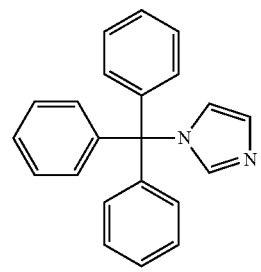

T86

The compounds will are referred to herein by their compound numbers as given above.

What is claimed is:

1. A method for deterring, inhibiting or reversing stenosis, restenosis or unwanted proliferation of an artery in a human or veterinary patient, said method comprising the step of:
administering to the patient a compound having the structural formula

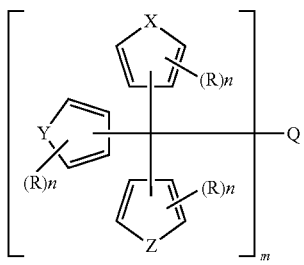

Wherein,
X, Y and Z are same or different and are independently selected from CH2, O, S, NR$_1$, N=CH, CH=N and R$_2$—C=C—R$_3$, where R$_2$ and R$_3$ are H or may combine to form a saturated or unsaturated carbocyclic or heterocyclic ring, optionally substituted with one or more R groups;
R$_1$ is selected from H, alkyl, alkenyl, alkynyl, cycloalkyl, aryl, acyl and aroyl, optionally substituted with hydroxy, amino, substituted amino, cyano, alkoxy, halogen, trihaloalkyl, nitro, thio, alkylthio, carboxy and alkoxycarbonyl groups;
R is selected from H, halogen, trihaloalkyl, hydroxy, acyloxy, alkoxy, alkenyloxy, thio, alkylthio, nitro, cyano, ureido, acyl, carboxy, alkoxycarbonyl, N—(R$_4$)(R$_5$) and saturated or unsaturated, chiral or achiral, cyclic or acyclic, straight or branched hydrocarbyl group with from 1 to 20 carbon atoms, optionally substituted with hydroxy, halogen, trihaloalkyl, alkylthio, alkoxy, carboxy, alkoxycarbonyl, oxoalkyl, cyano and N—(R$_4$)(R$_5$) group,
R$_4$ and R$_5$ are selected from H, alkyl, alkenyl, alkynyl, cycloalkyl and acyl or R$_4$ and R$_5$ may combine to form a ring, wherein a carbon may be optionally substituted by a heteroatom selected from O, S or N—R$_6$,
R$_6$ is H, alkyl, alkenyl, alkynyl, cycloalkyl, hydroxyalkyl or carboxyalkyl,
n is 1-5; m is 1 or 2; with the proviso that
when m is 1, Q is selected from OH, CN, carboxyalkyl, N—(R$_7$)(R$_8$), where R$_7$ and R$_8$ are selected from H, lower alkyl (1-4C), cycloalkyl, aryl, acyl, amido, or R$_7$ and R$_8$ may combine to form a saturated or unsaturated heterocyclic ring and optionally substituted with up to 3 additional heteroatoms selected from N, O, and S; or
—NH-heterocycle, where the heterocycle is represented by thiazole, oxazole, isoxazole, pyridine, pyrimidine, and purine and

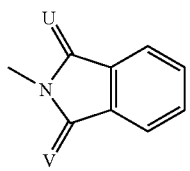

where U and V are selected from H and O; and
when m is 2, Q is a spacer of from 2-10 carbons as a straight or branched, chiral or achiral, cyclic or acyclic, saturated or unsaturated, hydrocarbon group, such as phenyl;

In the most preferred embodiment of this invention,
X, Y, and Z are R$_2$—C=C—R$_3$, where R$_2$ and R$_3$ are H;
R is selected from H and halogen, preferably, F and Cl;
m is 1; and
Q is —N—(R$_7$)(R$_8$), where R$_7$ and R$_8$ are selected from H, acyl, amido, and R$_7$ and R$_8$ combine to form a saturated or unsaturated heterocyclic ring, optionally substituted with up to three heteroatoms selected from N, O, or S, for example, pyrrolidine, piperidine, pyrazole, imidazole, oxazole, isoxazole, tetrazole, azepine, etc., which may be optionally substituted with a lower alkyl or amino group;
wherein the compound is administered at a dose that effectively deters, inhibits or reverses stenosis, restenosis or unwanted proliferation of an artery but does not inhibit hepatic cytochrome P450 enzyme activity.

2. A method according to claim 1 wherein the X, Y, and Z are each R$_2$—C=C—R$_3$; R$_2$ and R$_3$ are H; R is selected from H and halogen m is 2; and Q is a spacer of from 2-10 carbons either as a straight or branched hydrocarbon chain or as a containing a hydrocarbon ring.

3. A method according to claim 1 wherein the compound is 1-[(2-chlorophenyl)diphenylmethyl]-1H-pyrazole.

4. A method according to claim 1 wherein the compound is 1-[(2-fluorphenyl)diphenylmethyl]-1H-pyrazole.

5. A method according to claim 1 wherein the compound is 1-[(4-chlorophenyl)diphenylmethyl]-1H-pyrazole.

6. A method according to claim 1 wherein the compound is 1-[(2-fluorphenyl)diphenylmethyl]-1H-pyrazole.

7. A method according to claim 1 wherein the compound is 1-[(2-chlorophenyl)diphenylmethyl]-1H-1,2,3,4-tetrazole.

8. A method according to claim 1 wherein the compound is administered to the patient orally.

9. A method according to claim 1 wherein the compound is administered to the patient by injection.

10. A method according to claim 1 wherein the compound is administered to the patient transdermally.

11. A method according to claim 1 wherein the compound is administered to the patient transmucosally.

12. A method according to claim 1 wherein the compound is on or in an implantable device and wherein the compound is administered to the patient by implanting the device within the patient's body such that the compound elutes from the implanted device.

13. A method according to claim 12 wherein the device comprises a stent.

14. A method according to claim 13 wherein the stent is implanted in an artery of the patient such that a therapeutically effective amount of the compound elutes from the stent and deters reocclusion of the artery in which the stent is implanted.

15. A method according to claim 13 wherein the stent is implanted in a coronary artery of the patient such that a therapeutically effective amount of the compound elutes from the stent and deters reocclusion of the coronary artery in which the stent is implanted.

16. A method according to claim 1 wherein the compound is administered to a patient who has undergone or will undergo an angioplasty, atherectomy and/or stent implantation to treat an occluded blood vessel and wherein the compound is administered in an amount and by a route of administration that is effective to deter reocclusion of the blood vessel.

* * * * *